US012797040B2

(12) United States Patent
Masumoto

(10) Patent No.: US 12,797,040 B2
(45) Date of Patent: Nov. 17, 2026

(54) MEDICAL SUPPORT APPARATUS, OPERATING METHOD FOR MEDICAL SUPPORT APPARATUS, AND OPERATING PROGRAM

(71) Applicant: FUJIFILM CORPORATION, Tokyo (JP)

(72) Inventor: Jun Masumoto, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/809,358

(22) Filed: Aug. 20, 2024

(65) Prior Publication Data

US 2024/0407755 A1 Dec. 12, 2024

Related U.S. Application Data

(63) Continuation of application No. PCT/JP2023/003867, filed on Feb. 6, 2023.

(30) Foreign Application Priority Data

Feb. 28, 2022 (JP) ................................ 2022-030452

(51) Int. Cl.
*A61B 8/00* (2006.01)
*A61B 8/08* (2006.01)
*A61B 8/13* (2006.01)

(52) U.S. Cl.
CPC .............. *A61B 8/4245* (2013.01); *A61B 8/08* (2013.01); *A61B 8/13* (2013.01)

(58) Field of Classification Search
CPC ........... A61B 8/4245; A61B 8/08; A61B 8/13; A61B 2034/105; A61B 2090/309;
(Continued)

(56) References Cited

U.S. PATENT DOCUMENTS

2012/0294498 A1 11/2012 Popovic
2014/0303491 A1* 10/2014 Shekhar ................. G06T 7/337 600/424

(Continued)

FOREIGN PATENT DOCUMENTS

JP 2013-517031 A 5/2013
JP 2014-217745 A 11/2014

(Continued)

OTHER PUBLICATIONS

Extended European Search Report dated May 27, 2025, issued in corresponding EP Patent Application No. 23759661.4.

(Continued)

*Primary Examiner* — Michael J Carey
*Assistant Examiner* — Zainab Mohammed Aldarraji
(74) *Attorney, Agent, or Firm* — SOLARIS Intellectual Property Group, PLLC

(57) ABSTRACT

A processor acquires a surgical field image of a surgical field containing a target area inside the body and an ultrasound probe; acquire a first three-dimensional image based on an ultrasound image group; derive first positional relationship information indicating a position and orientation of the first three-dimensional image within the surgical field image; derive second positional relationship information indicating a positional relationship between a position within the first three-dimensional image and a position within a second three-dimensional image by performing image analysis on the first three-dimensional image and the second three-dimensional image, the second three-dimensional image having been generated on the basis of a tomographic image group; and generate a composite image with preparation information superimposed onto a corresponding position that corresponds to the target area within the surgical field
(Continued)

image on the basis of the first positional relationship information and the second positional relationship information.

18 Claims, 33 Drawing Sheets

(58) Field of Classification Search
CPC ........ A61B 2090/373; A61B 2090/378; A61B 8/466; A61B 8/5261; A61B 1/00; A61B 1/045; A61B 8/12; A61B 8/483; G06T 19/006; G06T 2207/10072; G06T 2207/10132; G06T 2207/30056; G06T 2207/30061; G06T 2207/30101; G06T 2207/30204; G06T 7/33
See application file for complete search history.

(56) References Cited

U.S. PATENT DOCUMENTS

| | | | | |
|---|---|---|---|---|
| 2014/0303499 | A1 | 10/2014 | Toma et al. | |
| 2017/0007350 | A1* | 1/2017 | Popovic | A61B 1/00165 |
| 2019/0290247 | A1 | 9/2019 | Popovic et al. | |
| 2021/0059700 | A1 | 3/2021 | Algawi et al. | |
| 2021/0298866 | A1 | 9/2021 | Cvetko et al. | |

FOREIGN PATENT DOCUMENTS

| | | |
|---|---|---|
| JP | 2016-202351 A | 12/2016 |
| JP | 2018-094020 A | 6/2018 |
| JP | 2019-517291 A | 6/2019 |

OTHER PUBLICATIONS

International Search Report issued in International Application No. PCT/JP2023/003867 on Apr. 4, 2023.

Written Opinion of the ISA issued in International Application No. PCT/JP2023/003867 on Apr. 4, 2023.

Extended European Search Report dated Sep. 14, 2026, issued in corresponding EP Application No. 26178704.8.

* cited by examiner

MEDICAL SUPPORT APPARATUS, OPERATING METHOD FOR MEDICAL SUPPORT APPARATUS, AND OPERATING PROGRAM

CROSS-REFERENCE TO RELATED APPLICATION

This application is a continuation application of International Application No. PCT/JP2023/003867, filed Feb. 6, 2023, the disclosure of which is incorporated herein by reference in its entirety. Further, this application claims priority from Japanese Patent Application No. 2022-030452 filed on Feb. 28, 2022, the disclosure of which is incorporated herein by reference in its entirety.

BACKGROUND

1. Technical Field

The technology of the present disclosure relates to a medical support apparatus, an operating method for a medical support apparatus, and an operating program.

2. Description of the Related Art

JP2018-94020A discloses a technology that uses an external sensor to acquire the position of an ultrasound probe in a surgical field and aligns an ultrasound image with a 3D image based on a tomographic image taken with a tomograph prior to surgery.

SUMMARY

The technology according to the present disclosure provides a medical support apparatus, an operating method for a medical support apparatus, and an operating program with which preparation information can be superimposed at an appropriate position within a surgical field image without using an external sensor.

A medical support apparatus according to the technology of the present disclosure includes a processor configured to: acquire a surgical field image obtained by optically taking, with a camera, an image of a surgical field containing a target area inside the body and an ultrasound probe inserted into the body; acquire a first three-dimensional image illustrating an internal structure of the target area, the first three-dimensional image being based on an ultrasound image group taken by the ultrasound probe; derive first positional relationship information indicating a position and orientation of the first three-dimensional image within the surgical field image, on the basis of pose information that indicates the position and orientation of the ultrasound probe within the surgical field as estimated by image analysis of the surgical field image; derive second positional relationship information indicating a positional relationship between a position within the first three-dimensional image and a position within a second three-dimensional image by performing image analysis on the first three-dimensional image and the second three-dimensional image, the second three-dimensional image indicating an internal structure of the target area and having been generated on the basis of a tomographic image group taken in advance by a tomograph; generate a composite image with preparation information superimposed onto the surgical field image, the preparation information having been prepared in advance as information related to the target area, including at least the second three-dimensional image or applied information applied to the second three-dimensional image, and having a defined three-dimensional position within the second three-dimensional image, the preparation information being superimposed onto a corresponding position that corresponds to the target area within the surgical field image on the basis of the first positional relationship information and the second positional relationship information; and control displaying of the composite image.

An operating method for a medical support apparatus according to the technology of the present disclosure is an operating method for a medical support apparatus including a processor configured to: acquire a surgical field image obtained by optically taking, with a camera, an image of a surgical field containing a target area inside the body and an ultrasound probe inserted into the body to take images of the inside of the target area; acquire a first three-dimensional image illustrating an internal structure of the target area, the first three-dimensional image having been generated on the basis of an ultrasound image group taken by the ultrasound probe; derive first positional relationship information indicating a position and orientation of the first three-dimensional image within the surgical field image, on the basis of pose information that indicates the position and orientation of the ultrasound probe within the surgical field as estimated by image analysis of the surgical field image; derive second positional relationship information indicating a positional relationship between a position within the first three-dimensional image and a position within a second three-dimensional image by performing image analysis on the first three-dimensional image and the second three-dimensional image, the second three-dimensional image indicating an internal structure of the target area and having been generated on the basis of a tomographic image group taken in advance by a tomograph; generate a composite image with preparation information superimposed onto the surgical field image, the preparation information having been prepared in advance as information related to the target area, including at least the second three-dimensional image or applied information applied to the second three-dimensional image, and having a defined three-dimensional position within the second three-dimensional image, the preparation information being superimposed onto a corresponding position that corresponds to the target area within the surgical field image on the basis of the first positional relationship information and the second positional relationship information; and control displaying of the composite image.

An operating program for a medical support apparatus according to the technology of the present disclosure is an operating program for causing a computer to function as a medical support apparatus, the operating program causing the computer to execute processing to: acquire a surgical field image obtained by optically taking, with a camera, an image of a surgical field containing a target area inside the body and an ultrasound probe inserted into the body to take images of the inside of the target area; acquire a first three-dimensional image illustrating an internal structure of the target area, the first three-dimensional image having been generated on the basis of an ultrasound image group taken by the ultrasound probe; derive first positional relationship information indicating a position and orientation of the first three-dimensional image within the surgical field image, on the basis of pose information that indicates the position and orientation of the ultrasound probe within the surgical field as estimated by image analysis of the surgical field image; derive second positional relationship information indicating a positional relationship between a position within the first three-dimensional image and a position within a second three-dimensional image by performing image analysis on the first three-dimensional image and the second three-dimensional image, the second three-dimensional image indicating an internal structure of the target area and having been generated on the basis of a tomographic image group taken in advance by a tomograph; generate a composite image with preparation information superimposed onto the surgical field image, the preparation information having been prepared in advance as information related to the target area, including at least the second three-dimensional image or applied information applied to the second three-dimensional image, and having a defined three-dimensional position within the second three-dimensional image, the preparation information being superimposed onto a corresponding position that corresponds to the target area within the surgical field image on the basis of the first positional relationship information and the second positional relationship information; and control displaying of the composite image.

BRIEF DESCRIPTION OF THE DRAWINGS

Exemplary embodiments according to the technique of the present disclosure will be described in detail based on the following figures, wherein:

FIG. 27 is a diagram illustrating a modification in which FIG. 26 is modeled by parallel projection;

FIG. 29 is a modification in which FIG. 28 is modeled by parallel projection;

DETAILED DESCRIPTION

First Embodiment

Figure 1:
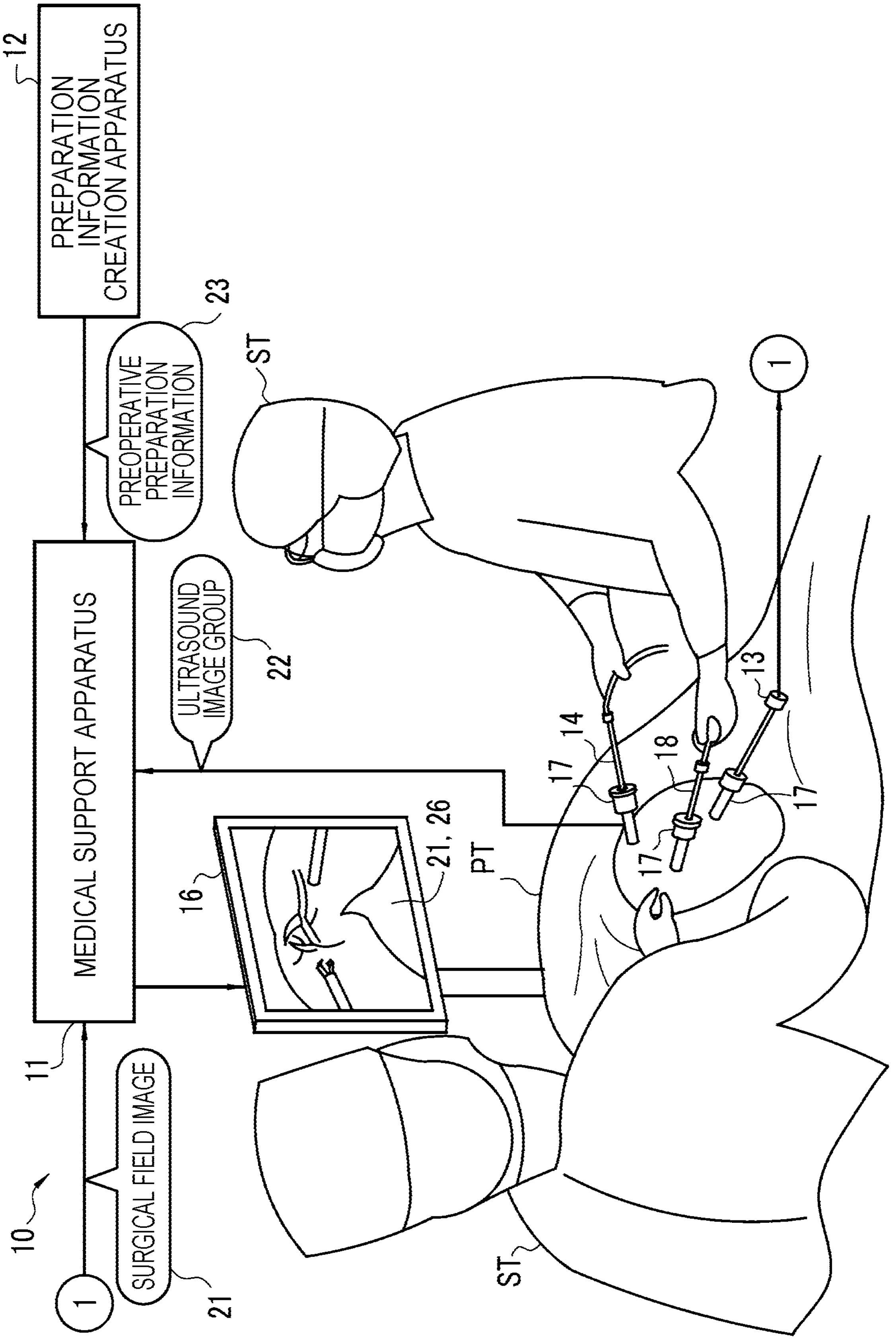
FIG. 1 is a diagram illustrating an overview of a medical support system including a medical support apparatus.
Figure 2:
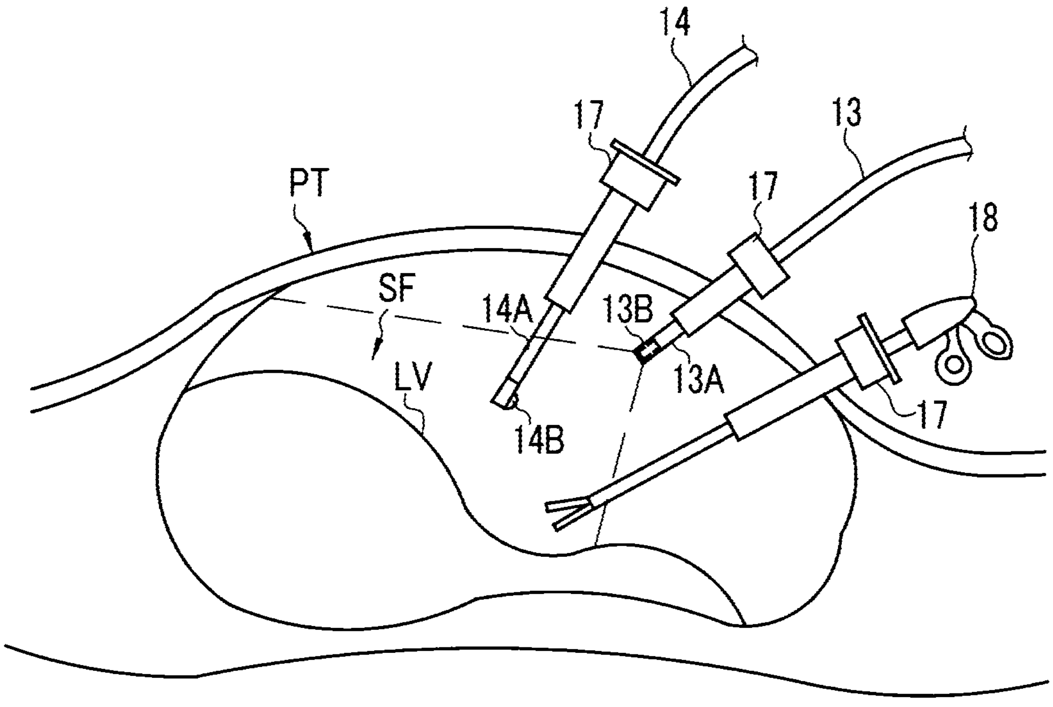
FIG. 2 is a diagram illustrating a state inside the body in specular surgery.

As illustrated in FIGS. 1 and 2, as one example, a medical support system 10 is used when performing specular surgery using an endoscope on a patient PT. The medical support system 10 provides, to medical staff ST including a physician, a visual field of the inside of the body of the patient PT, in addition to support information for supporting medical care such as surgery and examination. Such a medical support system 10 has a function for providing support information in real time during surgery, and thus is also referred to as a surgical navigation system or the like. The medical support system 10 includes a medical support apparatus 11 and a preparation information creation apparatus 12. The medical support apparatus 11 is an example of a "medical support apparatus" according to the technology of the present disclosure.

The medical support apparatus 11 is communicatively connected to an endoscope 13, an ultrasound probe 14, and a display 16. In specular surgery, a portion including the distal end part of each of the endoscope 13 and the ultrasound probe 14 are inserted into the body via trocars 17. The trocars 17 are insertion tools provided with an insertion hole through which the endoscope 13 or the like is inserted and a valve provided in the insertion hole to prevent gas leakage. In specular surgery, insufflation is performed by the injection of carbon dioxide gas into the abdominal cavity, and thus the trocars 17 are used to insert the endoscope 13, ultrasound probe 14, and the like into the body.

Also, in this example, the target area of surgery is the liver LV, and FIG. 2 illustrates how the endoscope 13 and the ultrasound probe 14 are inserted into the abdomen of the patient PT. Sign 18 is a treatment tool such as forceps, and the treatment tool is also inserted into the body via a trocar 17.

The endoscope 13 has an insertion part 13A to be inserted into the body of the patient PT, and the distal end part of the insertion part 13A has a built-in camera 13B and a light source (such as a light-emitting diode (LED)) for illumination. As an example, the endoscope 13 is a rigid endoscope with an inflexible insertion part 13A, also referred to as a laparoscope or the like due to being used often for abdominal cavity observation. The camera 13B includes an image sensor, such as a charge-coupled device (CCD) image sensor or a complementary metal-oxide-semiconductor (CMOS) image sensor, and imaging optics including a lens that forms a subject image on the image pick-up surface of the image sensor. The image sensor is capable of picking up color images, for example.

The endoscope 13 optically takes an image of a surgical field SF including a target area (in this example, the liver LV) inside the body of the patient PT. The endoscope 13 is connected to an endoscopic image processor, not illustrated, and the image processor to generates a surgical field image 21 by performing signal processing on the image pick-up signal outputted by the image sensor. Visible light such as white light is used as the illumination light for the endoscope 13, although in some cases special light such as ultraviolet rays and infrared light may be used. Note that special light such as ultraviolet rays and infrared light may also be used as the illumination light for the endoscope 13. Light restricted to a specific wavelength, such as short-wavelength narrow-band light in which light in a short-wavelength region such as the ultraviolet region is restricted to a narrow band, may be used as the special light. The surgical field image 21 is a video image of the surgical field SF illuminated by visible light, and more specifically is a video image based on reflected light generated by visible light being reflected near the surface of the surgical field SF. Accordingly, although superficial blood vessels that exist near the surface layer of the target area may be represented in some cases, internal structures such as vascular structures are difficult to observe in the surgical field image 21. The surgical field image 21 taken by the endoscope 13 is transmitted to the medical support apparatus 11 in real time via the endoscopic image processor.

The ultrasound probe 14 has an insertion part 14A to be inserted into the body of the patient PT, similarly to the endoscope 13, and the distal end part of the insertion part 14A has a built-in ultrasonic transducer 14B. The ultrasonic transducer 14B transmits ultrasonic waves to the target area and receives reflected waves that have reflected off the target area. The ultrasound probe 14 is connected to an ultrasound probe image processor, not illustrated. The ultrasound probe image processor uses a signal according to the reflected waves received by the ultrasound probe 14 as a basis for performing image reconstruction processing on the basis of the reflected waves. Through the image reconstruction processing, an ultrasound image 22A (see FIG. 6) illustrating the internal structure of the target area scanned by the ultrasound probe 14 is generated. The ultrasound image 22A is what is called a B-mode (brightness mode) image in which the internal structure of the target area, from the surface layer to deep layers reached by ultrasonic waves, is visualized as luminance information. The ultrasound image 22A allows for visualization of the internal structure of the target area that cannot be observed with the surgical field image 21 obtained by optical image-taking.

As one example, the ultrasound probe 14 is of the convex type that transmits ultrasonic waves radially, and a fan-shaped image with the ultrasonic transducer 14B as a base point is acquired. By causing the ultrasound probe 14 to scan, multiple ultrasound images 22A are taken along the scanning direction. These multiple ultrasound images 22A are collectively referred to as an ultrasound image group 22. The ultrasound image group 22 is transmitted to the medical support apparatus 11 in real time via the ultrasound probe image processor.

The medical support apparatus 11 acquires the surgical field image 21 from the endoscope 13 and acquires the ultrasound image group 22 from the ultrasound probe 14. If the ultrasound probe 14 and a treatment tool 18 are inserted into the surgical field SF, the ultrasound probe 14 and the treatment tool 18 appear in the surgical field image 21. The medical support apparatus 11 outputs the surgical field image 21 in which the ultrasound probe 14 and the treatment tool 18 appear to the display 16. Through the screen of the display 16, a visual field of the inside of the body of the patient PT is provided to the medical staff ST. A composite image 26 with preoperative preparation information 23 superimposed onto the surgical field image 21 is also displayed on the display 16. As described later, the composite image 26 is generated by the medical support apparatus 11.

The preparation information creation apparatus 12 is used to create the preoperative preparation information 23. The preparation information creation apparatus 12 is, for example, a computer in which is installed an image processing program having image processing functions for three-dimensional images. As described later, as one example, the preoperative preparation information 23 is surgical planning information or the like created prior to surgery. Also, as one example, the preoperative preparation information 23 is created by the medical staff ST using the preparation information creation apparatus 12 prior to surgery.

The medical support apparatus 11 acquires the preoperative preparation information 23 from the preparation information creation apparatus 12. The medical support apparatus 11 creates the composite image 26 with the preoperative preparation information 23 superimposed onto the surgical field image 21, and outputs the generated composite image 26 to the display 16. Through the screen of the display 16, the preoperative preparation information 23 is provided to the medical staff ST.

An example of the preoperative preparation information 23 will be described with reference to FIGS. 3 and 4. The preoperative preparation information 23 is created on the basis of a tomographic image group 32 taken in advance by a tomograph 31 such as a computed tomography (CT) apparatus or a magnetic resonance imaging (MRI) apparatus. In the case where the tomograph 31 is a CT apparatus, CT values are acquired while a radiation source and a radiation detector are rotated around the body axis of the patient PT. CT values are acquired at each position in the body axis direction by causing the radiation source and radiation detector to scan in the body axis direction of the patient PT. CT values are values of radiation absorption inside the body of the patient PT. The tomograph 31 generates tomographic images 32A by performing image reconstruction processing on the basis of the CT values acquired in each direction around the body axis. Each tomographic image 32A is a two-dimensional image generated according to the slice thickness in the body axis direction, and the tomographic image group 32 is the set of multiple tomographic images 32A corresponding to each position in the body axis direction. The tomographic image group 32 is outputted to an image database 33 such as a picture archiving and communication system (PACS).

On the basis of the tomographic image group 32 obtained by the tomograph 31, the preparation information creation apparatus 12 generates a three-dimensional image 34, which is a set of voxel data 34A, by performing three-dimensional (3D) modeling to numerically describe the three-dimensional shape of the body of the patient PT. The voxel data 34A is in units of pixels in a three-dimensional space, with each pixel having three-dimensional coordinate information and a pixel value. The three-dimensional image 34 generated by 3D modeling is also referred to as three-dimensional volume data or the like. In the tomographic image group 32, the pixel spacing of each tomographic image 32A and the slice thickness of each tomographic image 32A may differ from one another. In this case, for example, in the 3D modeling, interpolation processing between adjacent tomographic images 32A may be performed to generate a three-dimensional image 34 with isotropic voxel data 34A in which the length is equal in each direction of the three dimensions. The three-dimensional image 34 generated on the basis of the tomographic image group 32 is information created prior to surgery, and thus is referred to as the preoperative 3D image 34 out of convenience herein. The preoperative 3D image 34 is an example of a "second three-dimensional image" according to the technology of the present disclosure.

The preoperative 3D image 34 is an image that can reproduce the external shape of the body of the patient PT, anatomical areas such as organs inside the body, and internal structures of such areas. The preoperative 3D image 34 illustrated in FIG. 3 illustrates data on the liver LV as one example of an anatomical area. The preoperative 3D image 34 also includes data that can reproduce the vascular structure, which is one example of an internal structure of the liver LV.

Also, the preoperative 3D image 34 in this example is a color image, and a pixel value for each of red (R), green (G), and blue (B) is given as the pixel value of the voxel data 34A. Note that the preoperative 3D image 34 may also be a monochrome image. For example, the pixel value of the voxel data 34A may be represented solely by the luminance (Y) based on a CT value. The value used as the pixel value of the voxel data 34A may also be converted from a CT value using a preset lookup table (LUT) or calculation formula. The pixel value of voxel data 34A may also be set to a color associated with each specific area, such as an organ or lesion identified in the preoperative 3D image 34. Opacity is also set in the voxel data 34A. Opacity is data used in volume rendering. Rendering is processing to convert a portion of the preoperative 3D image 34 into a two-dimensional projected image, and volume rendering is a rendering technique that also projects internal information about an object included in the preoperative 3D image 34 onto the projected image. Setting the opacity for each piece of the voxel data 34A makes it possible to represent internal information in different ways, such as projecting internal information onto the projected image in an opaque manner, a translucent manner, and a transparent manner, when performing volume rendering.

Figure 4:
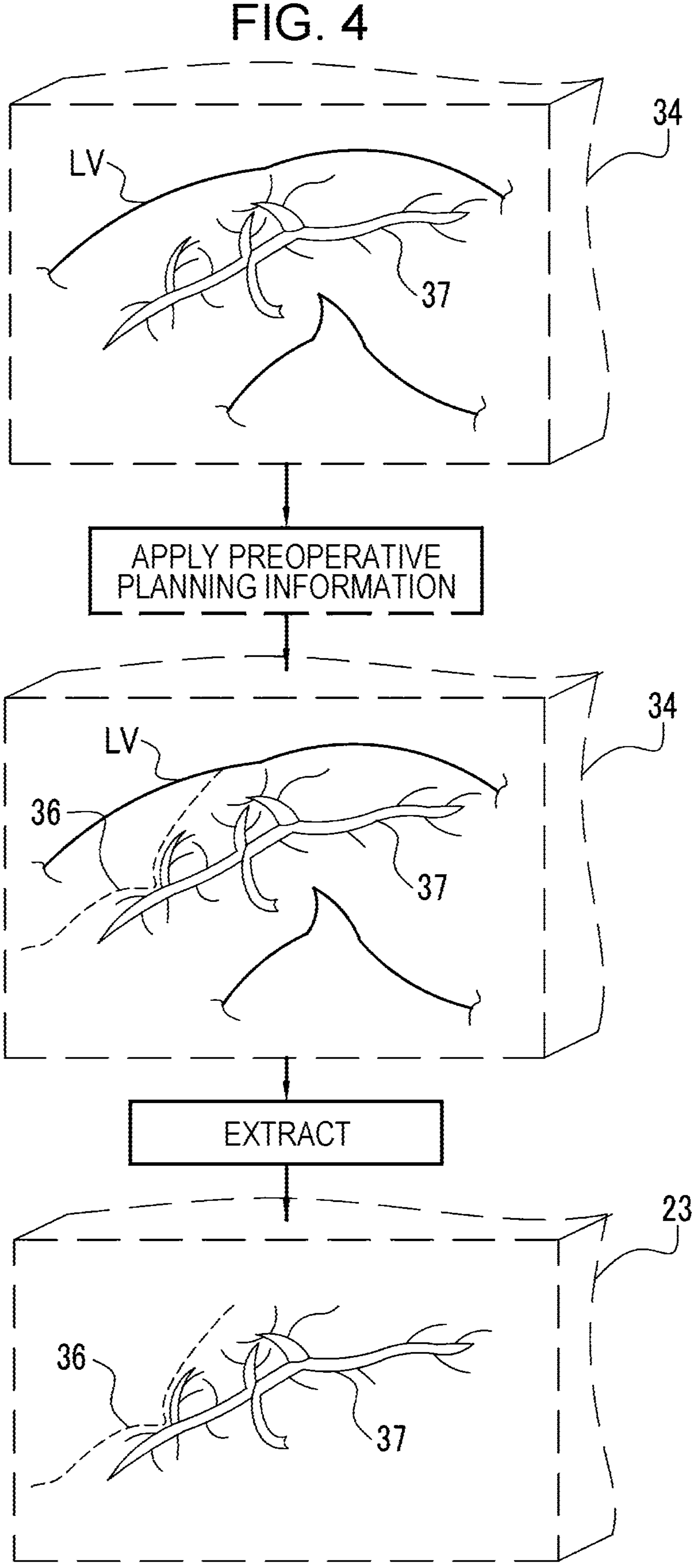
FIG. 4 is a diagram of a method of creating preoperative preparation information.

As illustrated in FIG. 4, the preoperative preparation information 23 is generated on the basis of the preoperative 3D image 34. The preoperative preparation information 23 is an example of "preparation information" according to the technology of the present disclosure, and is preparation information that is prepared in advance as information related to the target area on which surgery is to be performed. The preoperative preparation information 23 includes a surgical plan as one example. Surgical planning information is information formulated through simulation performed prior to surgery, for example. In FIG. 4, the case in which the target area of surgery is the liver LV and the treatment is to perform surgery to excise a portion of the liver LV is explained as an example. The surgical planning information in the case of excising the liver LV includes an excision line 36 indicating the position of excision, for example. Such an excision line 36 is applied to the preoperative 3D image 34 as the preoperative preparation information 23. The excision line 36 is an example of "applied information" according to the technology of the present disclosure. Besides applied information, the preoperative preparation information 23 may also include the internal structure of the target area. In the example of FIG. 4, a vascular structure 37 is illustrated as the internal structure of the liver LV. The preoperative preparation information 23 including such an excision line 36 and vascular structure 37 extracted from the preoperative 3D image 34.

In this way, the preoperative preparation information 23 is preparation information which is prepared in advance as information related to the target area, which includes at least the preoperative 3D image 34 or applied information applied to the preoperative 3D image 34, and which has a defined three-dimensional position within the preoperative 3D image 34. Also, since the preoperative preparation information 23 is information based on the preoperative 3D image 34, a plurality of pieces of preoperative preparation information 23 at different depths in the depth direction proceeding from the surface layer to the deep layers of the target area in the preoperative 3D image 34 is included. The plurality of pieces of preoperative preparation information 23 may be information pertaining to a plurality of regions which have been morphologically dissociated from each other, or a plurality of regions in a single area, such as a plurality of regions of the vascular structure 37. The inclusion of a plurality of pieces of preoperative preparation information 23 at different depths in this way makes it possible to provide more detailed preoperative preparation information 23 in accordance with the depth of the target area.

Figure 5:
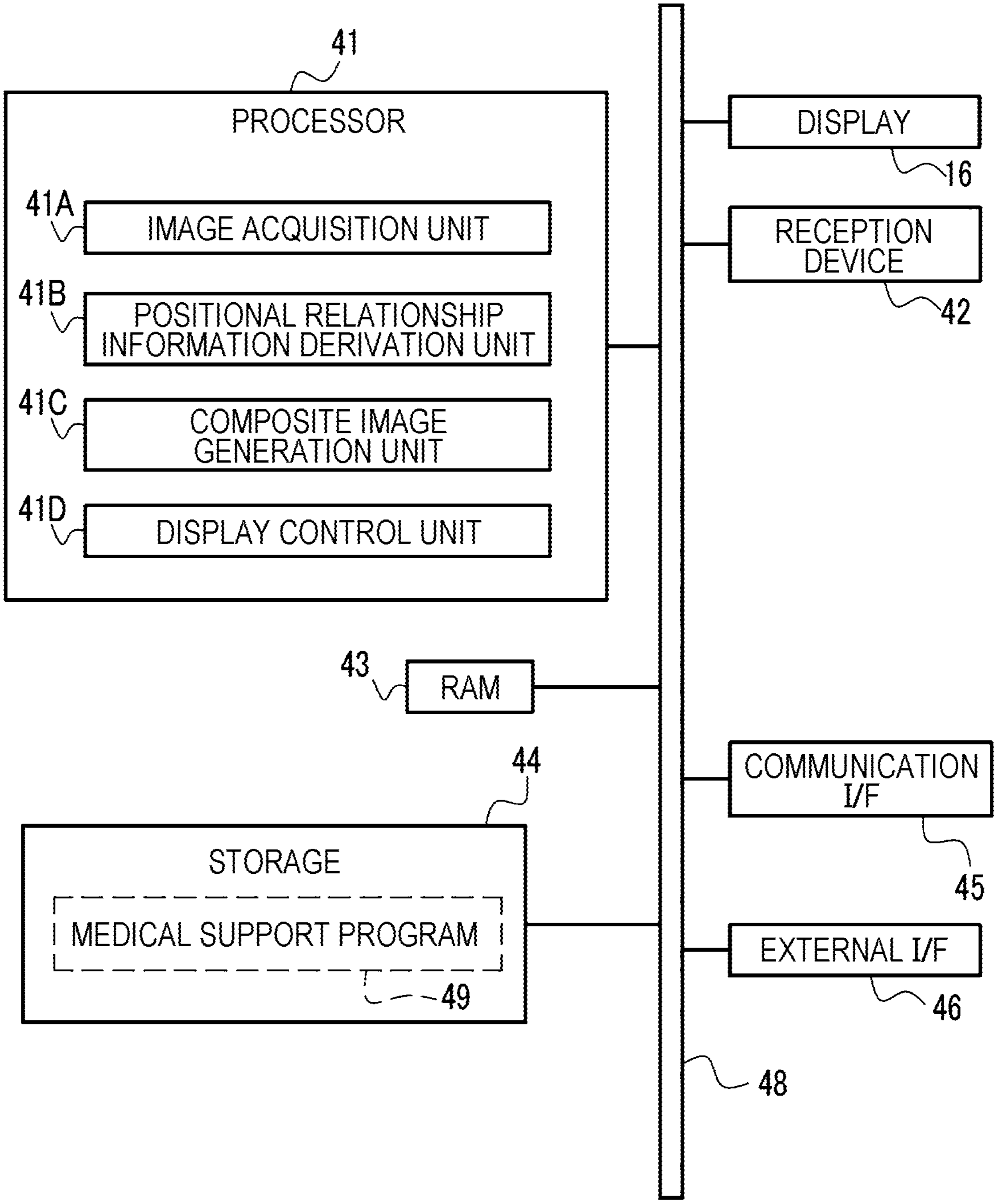
FIG. 5 is a diagram illustrating a hardware configuration of a medical support apparatus.

FIG. 5 illustrates an example of a hardware configuration of the medical support apparatus 11. The medical support apparatus 11 is an example of a "medical support apparatus" and a "computer" according to the technology of the present disclosure, and includes a processor 41, a reception device 42, the display 16, random access memory (RAM) 43, storage 44, a communication I/F 45, and an external I/F 46. These components are connected to a bus 48 and can communicate with one another.

The medical support apparatus 11 is operated through the reception device 42 by an operator such as the medical staff ST. The reception device 42 includes a keyboard, mouse, and the like, not illustrated, and accepts instructions from the operator. The reception device 42 may also be a device such as a touch panel that receives touch input, a device such as a microphone that receives voice input, a device such as a camera that receives gesture input, and the like.

The display 16 may be an electro-luminescence (EL) display or a liquid crystal display, for example. Besides the surgical field image 21 and the composite image 26, various information is displayed on the display 16.

The processor 41 is a central processing unit (CPU), for example, centrally controls each component of the medical support apparatus 11 by following a control program, and executes various processes by following various application programs.

The storage 44 is a non-volatile storage apparatus storing various programs, various parameters, and the like. The storage 44 may be a hard disk drive (HDD) and a solid state drive (SSD), for example. Also, the storage 44 stores a medical support program 49 for causing the computer to function as the medical support apparatus 11.

The RAM 43 is a memory in which information is stored temporarily, and is used as work memory by the processor 41. The RAM 43 may be dynamic random access memory (DRAM) or static random access memory (SRAM), for example.

The communication I/F is connected to a network (omitted from illustration) such as a local area network (LAN) and/or a wide area network (WAN), and controls transmission by following a communication protocol defined by any of various wired or wireless communication standards.

The external I/F 46 is a Universal Serial Bus (USB) interface, for example, and is used to connect with peripheral equipment such as printers and memory cards.

The processor 41 performs a medical support process by reading out the medical support program 49 from the storage 44 and executing the medical support program 49 in the RAM 43. The medical support process is achieved by the processor 41 operating as an image acquisition unit 41A, a positional relationship information derivation unit 41B, a composite image generation unit 41C, and a display control unit 41D. The medical support program 49 is an example of a "medical support program" according to the technology of the present disclosure.

The image acquisition unit 41A acquires the surgical field image 21 and the ultrasound image group 22. For example, the surgical field image 21 and/or the ultrasound image group 22 are acquired via the external I/F 46 or the communication I/F 45 from an apparatus that includes the processor of the endoscope 13 and/or the processor of the ultrasound probe 14. Note that the processor of the endoscope 13 and/or the processor of the ultrasound probe 14 may be included in the medical support apparatus 11, or there may be a database storing the surgical field image 21 and/or the ultrasound image group 22 generated by an apparatus that includes the processor the endoscope 13 and/or the processor of the ultrasound probe 14, and the surgical field image 21 and/or the ultrasound image group 22 may be acquired from the database. The image acquisition unit 41A also acquires the preoperative preparation information 23 including the preoperative 3D image 34. For example, the preoperative preparation information 23 is acquired from the preparation information creation apparatus 12 via the external I/F 46 or the communication I/F 45. Note that the preparation information creation apparatus 12 and the medical support apparatus 11 may be a unified apparatus, or there may be a database storing the preoperative preparation information 23 generated by the preparation information creation apparatus 12, and the preoperative preparation information 23 may be acquired from the database.

The positional relationship information derivation unit 41B performs image analysis on the surgical field image 21, the preoperative 3D image 34, and the like to thereby derive first positional relationship information 58 (see FIGS. 13 and 14) and second positional relationship information 59 (see FIG. 15) described later. The composite image generation unit 41C generates the composite image 26 by performing processing to superimpose the preoperative preparation information 23 onto the surgical field image 21. The display control unit 41D controls the display of the composite image 26 on the display 16.

The processor 41 superimposes the preoperative preparation information 23 onto a corresponding position that corresponds to the target area in the surgical field image 21. The corresponding position includes the target area and the surroundings thereof. As illustrated in FIG. 4, the preoperative preparation information 23 in this example is the excision line 36 of the liver LV and the vascular structure 37 internal to the liver LV. The surgical field image 21 provides a visual field of the inside of the body of the patient PT to the medical staff ST performing surgery. By providing the composite image 26 in which the excision line 36, which is one example of surgical planning information, is superimposed onto the surgical field image 21, the medical staff ST can clearly recognize the position to excise. Also, as described above, it is difficult to observe the internal structure of the target area with the surgical field image 21. Accordingly, by providing the composite image 26 in which the vascular structure 37 or other internal structure is superimposed onto the surgical field image 21, the medical staff ST can clearly recognize the positions of blood vessels.

To make such preoperative preparation information 23 useful support information, it is necessary to align the preoperative preparation information 23 at an appropriate position within the surgical field image 21. For example, the excision line 36 and vascular structure 37 of the liver LV are preferably displayed at a corresponding position that corresponds to the liver LV within the surgical field image 21. In the past, such alignment has been performed by using an external sensor such as a magnetic sensor.

The processor 41 of the medical support apparatus 11 according to the present disclosure aligns the surgical field image 21 and the preoperative preparation information 23 through image analysis, without using an external sensor. The following specifically describes processing to generate the composite image 26 through alignment by image analysis.

(Acquisition of First Three-Dimensional Image)

The processor 41 acquires an ultrasound three-dimensional (3D) image 51 based on the ultrasound image group 22 taken by the ultrasound probe 14. The processor 41 uses the ultrasound 3D image 51 acquired during surgery for alignment. The ultrasound 3D image 51 is an example of a "first three-dimensional image" according to the technology of the present disclosure.

Figure 6:
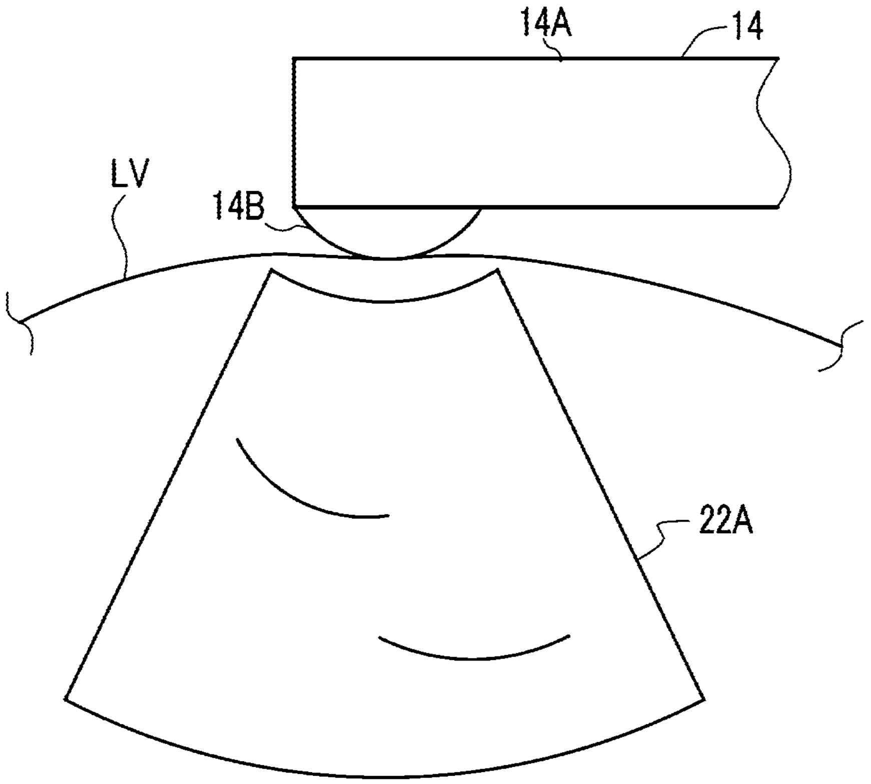
FIG. 6 is a diagram of an ultrasound probe and an ultrasound image.
Figure 7:
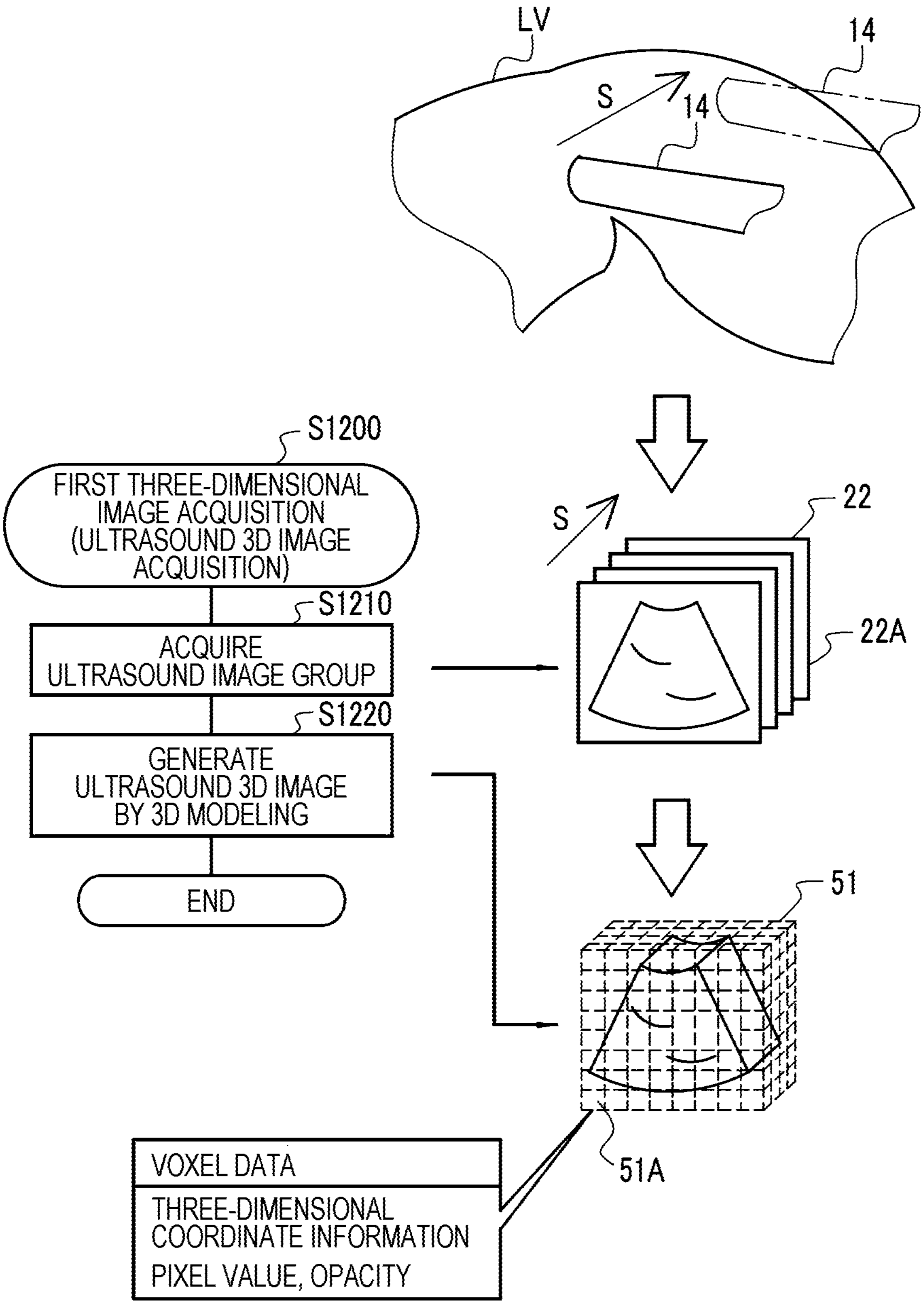
FIG. 7 is a diagram of a procedure for generating an ultrasound 3D image.

As illustrated in FIGS. 6 and 7, first, the ultrasound probe 14 is made to scan along the surface of a target area such as the liver LV, thereby allowing the acquisition of an ultrasound image 22A at each position along a scanning trajectory S. The processor 41 generates the ultrasound 3D image 51 by executing the processing in step S1200 illustrated in FIG. 7. Step S1200 includes a sub-step S1210 of acquiring the ultrasound image group 22 and a sub-step S1220 of generating the ultrasound 3D image 51 by performing 3D modeling on the basis of the acquired ultrasound image group 22. The ultrasound images 22A are tomographic images similar to the tomographic images 32A illustrated in FIG. 3, and the ultrasound image group 22 is similar to the tomographic image group 32. Internal structures of the target area, such as the vascular structure 37 of the liver LV, are likewise represented in the ultrasound image group 22.

Figure 3:
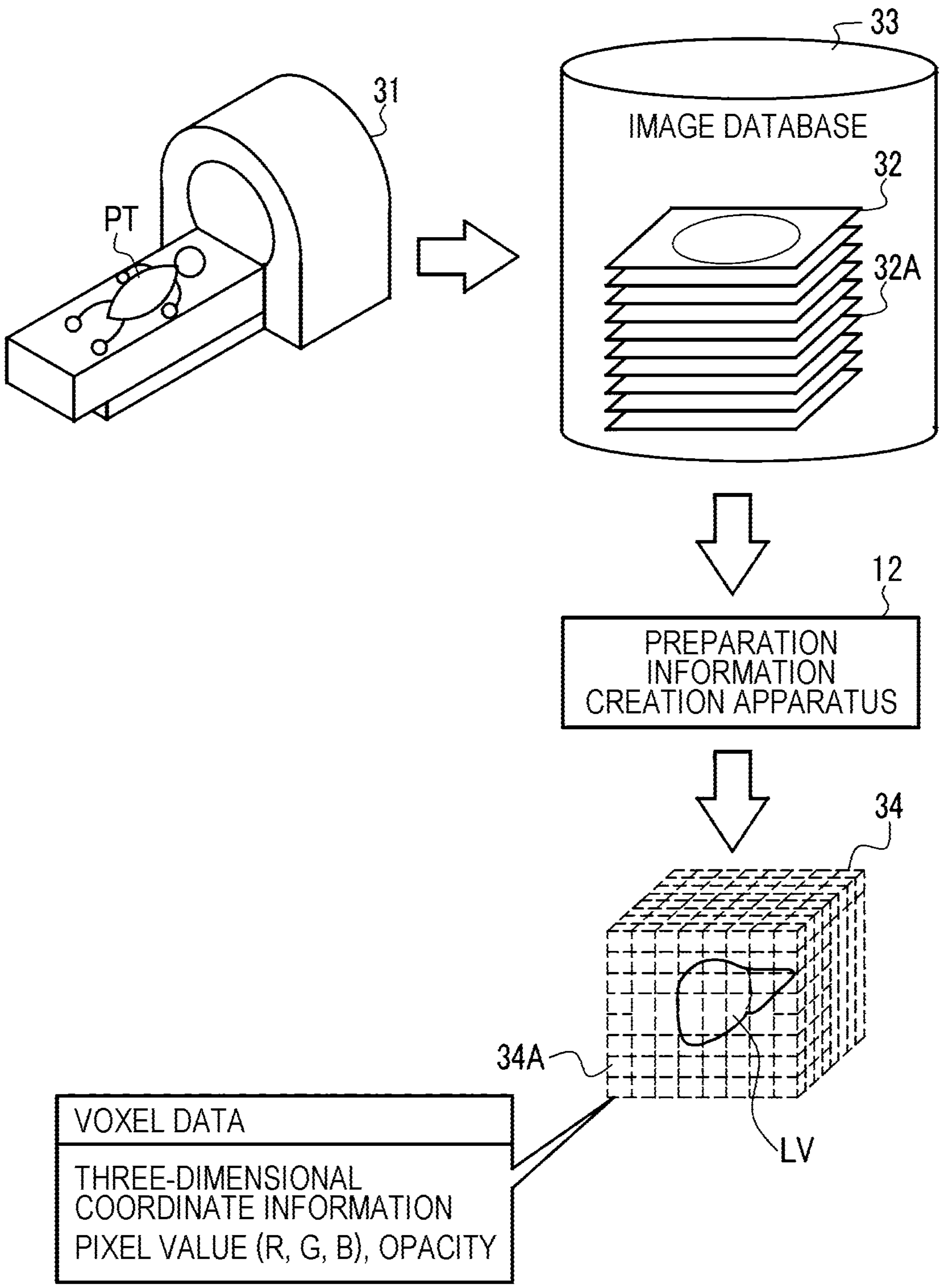
FIG. 3 is a diagram of a method of creating a preoperative 3D image.

The processor 41 generates the ultrasound 3D image 51 by executing processing similar to the 3D modeling described in FIG. 3. Like the preoperative 3D image 34, the ultrasound 3D image 51 is a set of voxel data 51A, each piece of which is a pixel in a three-dimensional space. The voxel data 51A is also similar to the voxel data 34A illustrated in FIG. 3, with three-dimensional coordinates, a pixel value, and opacity set therein.

Derivation of First Positional Relationship Information

Figure 8:
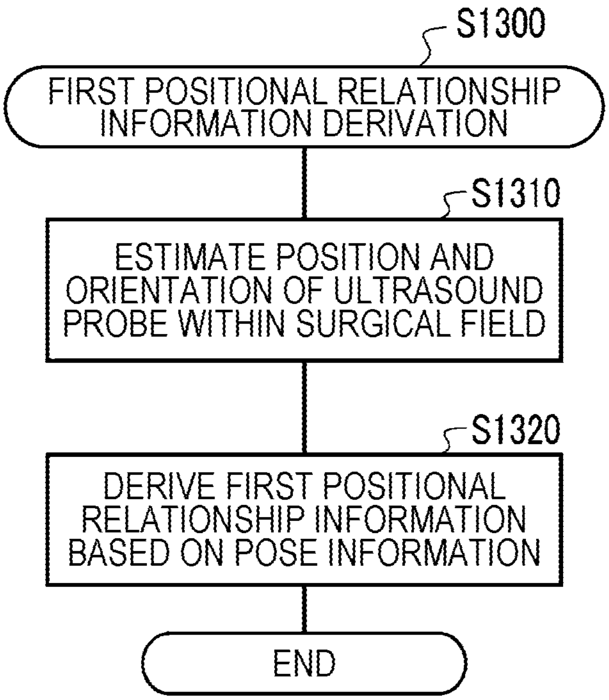
FIG. 8 is a flowchart illustrating a procedure for deriving first positional relationship information.

FIGS. 8 to 14 will be used to describe processing to derive the first positional relationship information 58. First, as illustrated in FIG. 8, the processor 41 derives the first positional relationship information 58 by executing the processing in step S1300. Step S1300 includes a sub-step S1310 of estimating the position and orientation of the ultrasound probe 14 within the surgical field SF, and a sub-step S1320 of deriving the first positional relationship information 58 on the basis of estimated pose information 57.

FIGS. 9 to 12 is a diagram conceptually explaining the processing in sub-step S1310. The processor 41 estimates the position and orientation of the ultrasound probe 14 within the surgical field SF by performing image analysis on the surgical field image 21.

Figure 9:
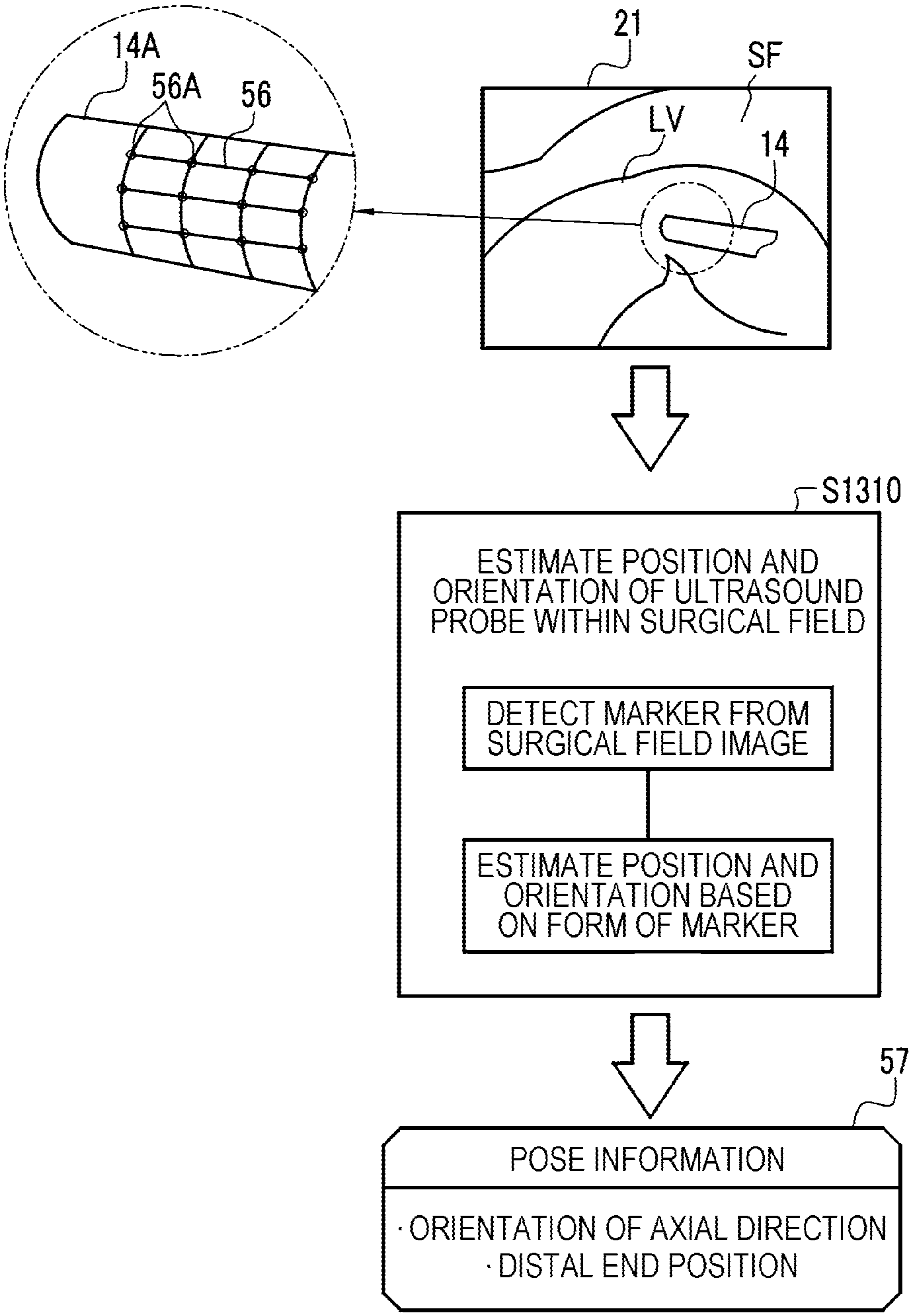
FIG. 9 is a diagram illustrating a procedure for deriving pose information.

As illustrated in FIG. 9, as one example, a marker 56 formed from an optically detectable pattern is provided on the outer circumferential surface of the ultrasound probe 14. The processor 41 estimates the position and orientation of the ultrasound probe 14 within the surgical field SF by detecting the marker 56 from the surgical field image 21. As one example, the marker 56 is a lattice marker formed by first lines extending in the axial direction of the insertion part 14A of the ultrasound probe 14 and second lines formed orthogonally to the axial direction and in the circumferential direction along the outer circumferential surface of the insertion part 14A. The lattice spacing of the marker 56 is fixed. Sign 56A indicates the plurality of intersection points between the first and second lines.

In sub-step S1310, the processor 41 detects the marker 56 from the surgical field image 21. The processor 41 then estimates the position and orientation of the ultrasound probe 14 on the basis of the form of the marker 56, and derives pose information 57. The pose information 57 includes the orientation of the axial direction of the ultrasound probe 14 and the distal end position where the ultrasonic transducer 14B is provided in the ultrasound probe 14.

Figure 10:
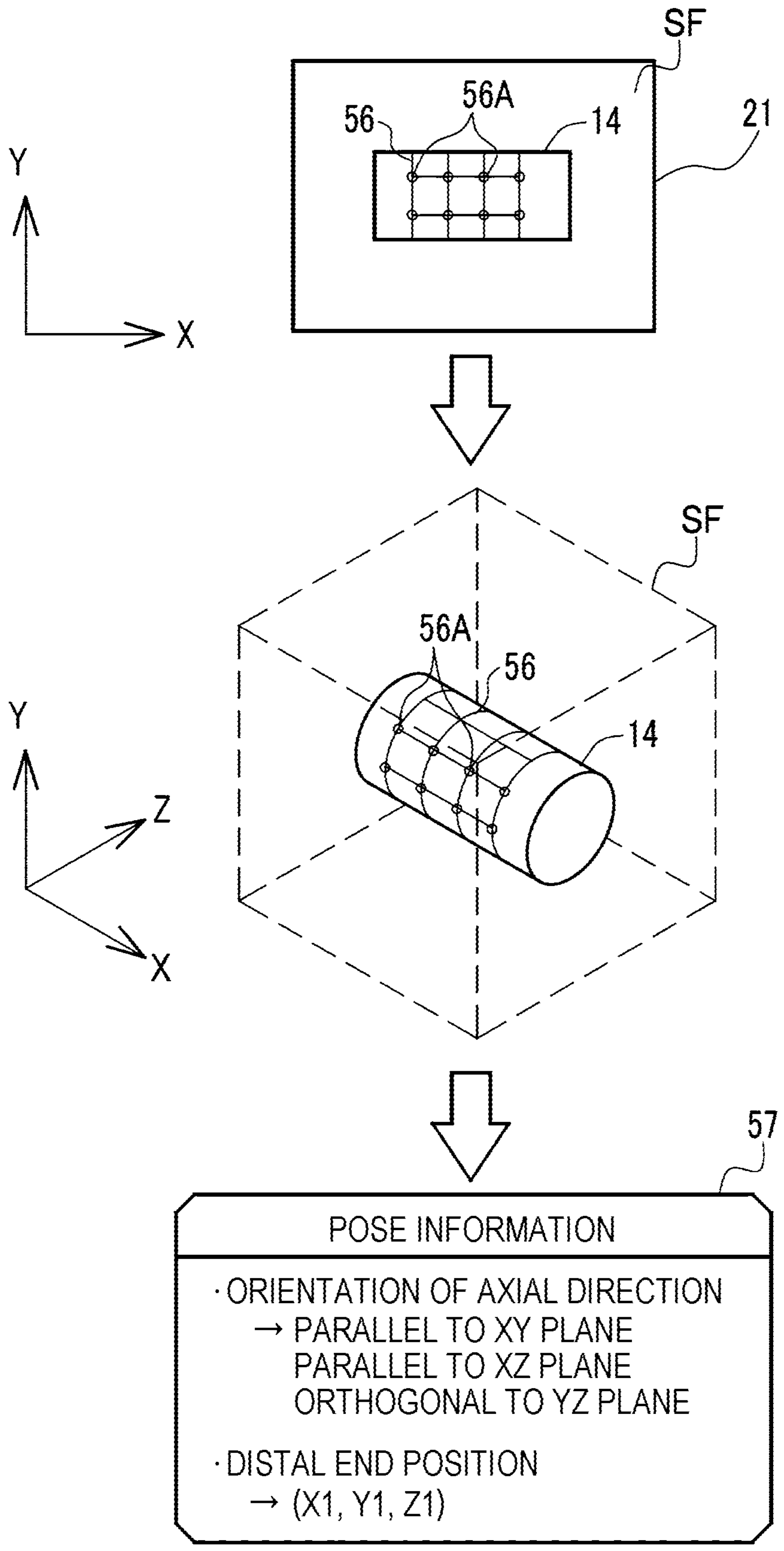
FIG. 10 is a diagram illustrating a first example of the position and orientation of an ultrasound probe.
Figure 11:
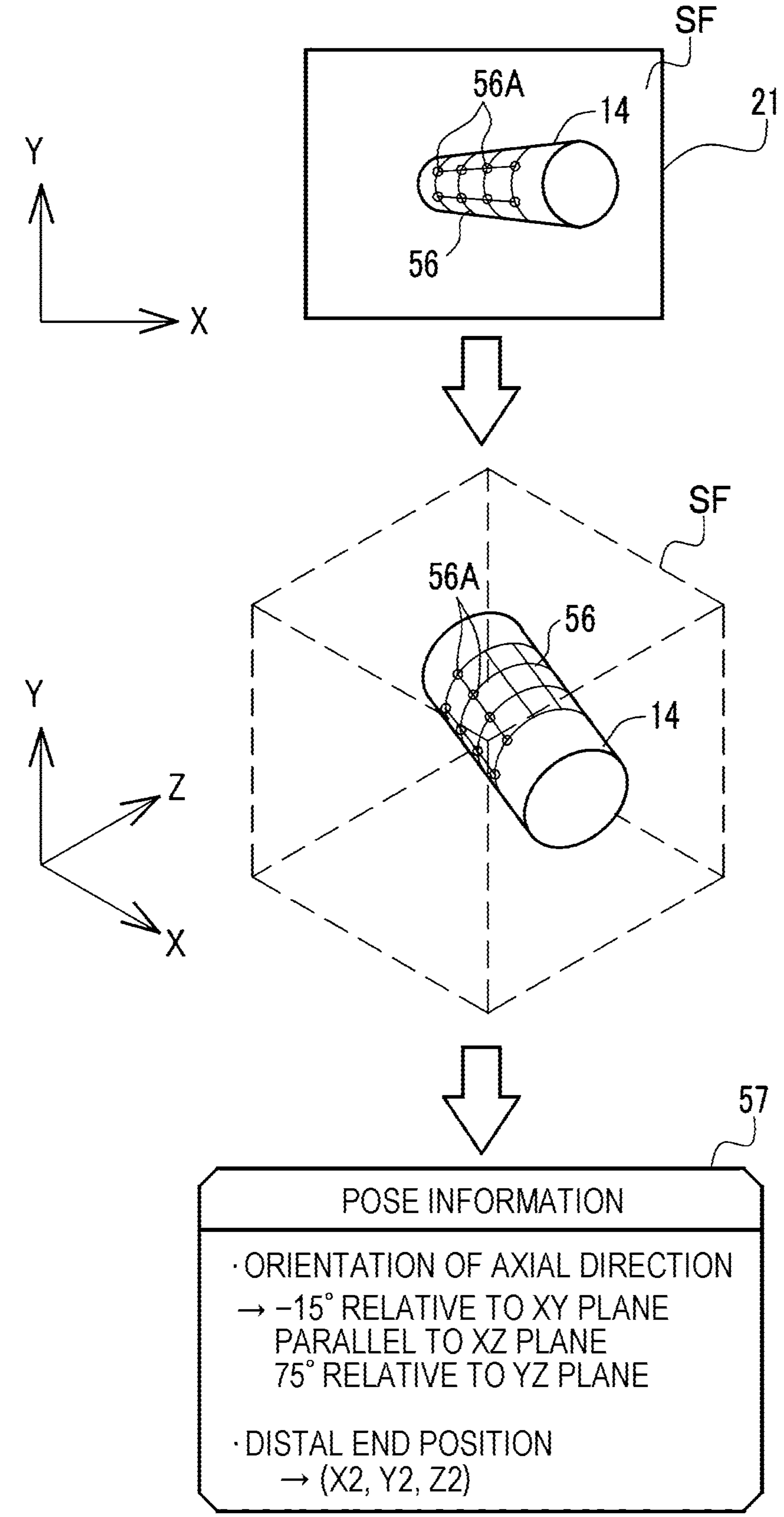
FIG. 11 is a diagram illustrating a second example of the position and orientation of an ultrasound probe.

FIGS. 10 and 11 illustrates positional relationships between the position and orientation of the ultrasound probe 14 within the surgical field image 21 and the position and orientation of the ultrasound probe 14 within the surgical field SF defined as three-dimensional space. The Z axis of the surgical field SF, that is, the three-dimensional space, is the direction parallel to the image-taking optical axis of the camera 13B of the endoscope 13, while the XY plane is the plane parallel to the image pick-up surface of the camera 13B, and is orthogonal to the image-taking optical axis. The XY plane is parallel to the picture plane of the surgical field image 21. Note that FIGS. 10 and 11 are conceptual diagrams, and out of convenience, illustrate only the distal end portion of the ultrasound probe 14 where the marker 56 is formed. The same applies to FIG. 12 and subsequent drawings.

FIG. 10 illustrates a state in which the axial direction of the ultrasound probe 14 within the surgical field SF as the three-dimensional space is orthogonal to the image-taking optical axis of the camera 13B of the endoscope 13 (more specifically, a state in which the axial direction is parallel to the X axis). When the ultrasound probe 14 is in such an orientation, the orthogonal lines of the marker 56 in the surgical field image 21 are parallel to the X axis and the Y axis, respectively, and the spacing between adjacent intersection points 56A is also the same.

FIG. 11 illustrates a state in which the axial direction of the ultrasound probe 14 within the surgical field SF as the three-dimensional space is not orthogonal to the image-taking optical axis, but is inclined in the depth direction parallel to the image-taking optical axis. The orientation illustrated in FIG. 11 is a state in which the ultrasound probe 14 has been rotated approximately 15° around the Y axis from the orientation illustrated in FIG. 10. When the ultrasound probe 14 is in such an orientation, the lines extending in the circumferential direction from among the lattice lines of the marker 56 in the surgical field image 21 are shorter farther away from the camera 13B in the depth direction. Furthermore, the spacing between adjacent intersection points 56A is similar, with the spacing between intersection points 56A being shorter at positions farther away from the camera 13B.

In this way, the form of the marker 56 appearing in the surgical field image 21 changes depending on the orientation of the ultrasound probe 14. The processor 41 detects the orientation of the ultrasound probe 14 on the basis of such a form of the marker 56 within the surgical field image 21. Also, the relative positional relationship between the marker 56 and the distal end position of the ultrasound probe 14 is known. The processor 41 detects the distal end position of the ultrasound probe 14 within the surgical field SF on the basis of the detected position of the marker 56 in the surgical field image 21 and the known positional relationship between the marker 56 and the distal end position of the ultrasound probe 14.

The pose information 57 in the example in FIG. 10 is, for example, information in which the orientation of the axial direction of the ultrasound probe 14 is parallel to the XY and XZ planes, and orthogonal to the YZ plane. The pose information 57 in the example in FIG. 11 is, for example, information in which the orientation of the axial direction of the ultrasound probe 14 is −15° with respect to the XY plane, parallel to the XZ plane, and 75° with respect to the YZ plane.

Figure 12:
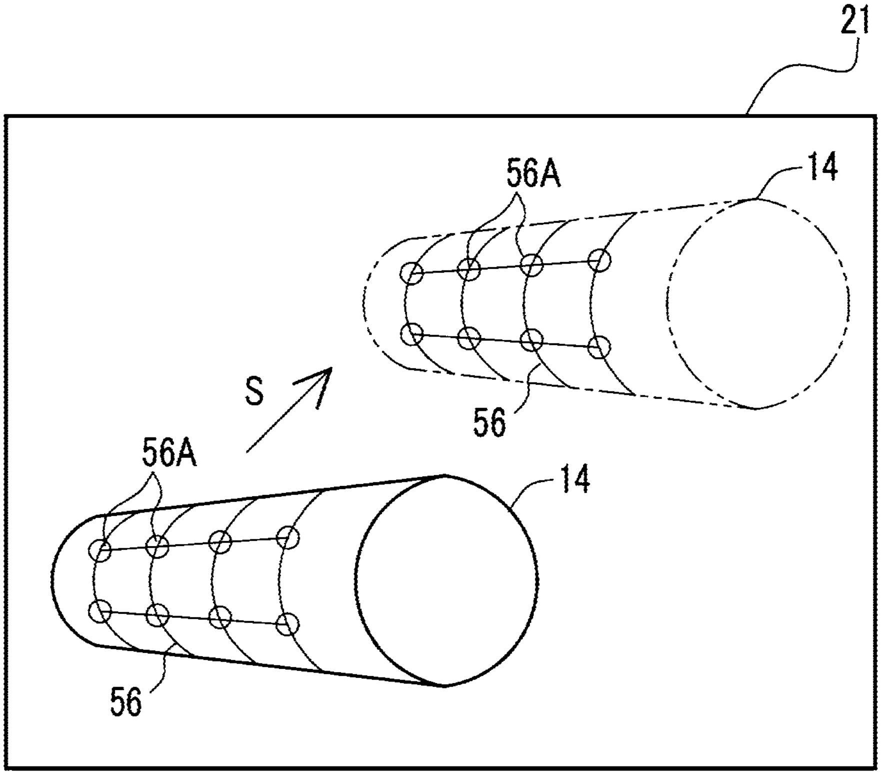
FIG. 12 is a diagram illustrating how an ultrasound probe moves during a scan.

Furthermore, as illustrated in FIG. 12, the processor 41 detects the scanning trajectory S of the ultrasound probe 14 by using a plurality of surgical field images 21 taken at different times. The processor 41 determines the trajectory along which the 56 moves as the scanning trajectory S of the ultrasound probe 14, on the basis of the position of the marker 56 in the plurality of surgical field images 21. As one example, the scanning trajectory S is used for alignment when layering a plurality of ultrasound images 22A acquired by the ultrasound probe 14. In the tomograph 31 illustrated in FIG. 3, the scanning direction is the body axis direction and the scanning trajectory is defined mechanically as a straight line. Accordingly, when layering a plurality of acquired tomographic images 32A, if the center positions of the tomographic images 32A are aligned with each other, no misalignment occurs among the tomographic images 32A. In contrast, since the scanning of the ultrasound probe 14 is performed manually, the scanning trajectory S is not necessarily a perfectly straight line. Accordingly, when layering a plurality of ultrasound images 22A, it is necessary to align the plurality of ultrasound images 22A on the basis of the scanning trajectory S.

Figure 13:
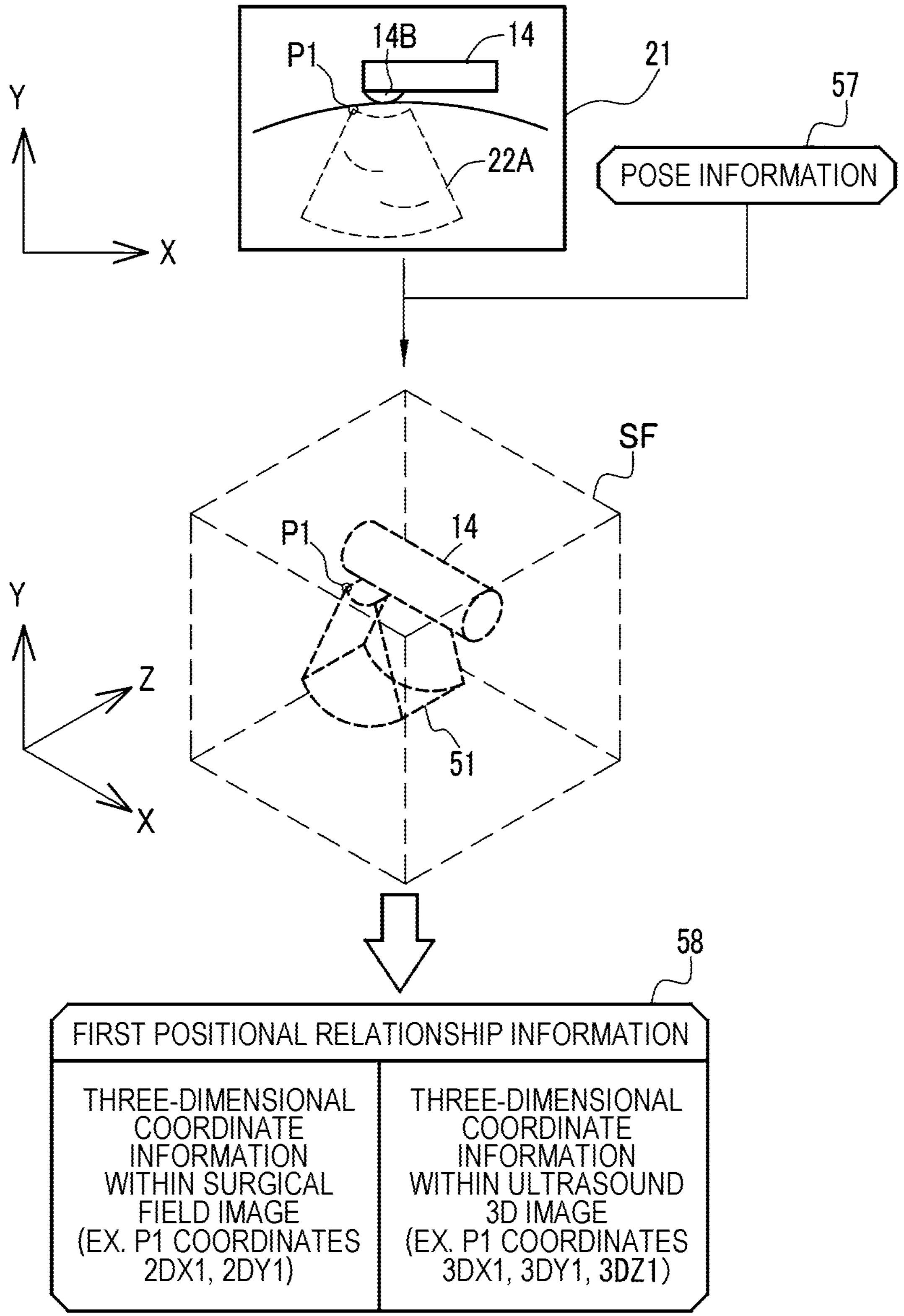
FIG. 13 is a diagram illustrating a first example of first positional relationship information.
Figure 14:
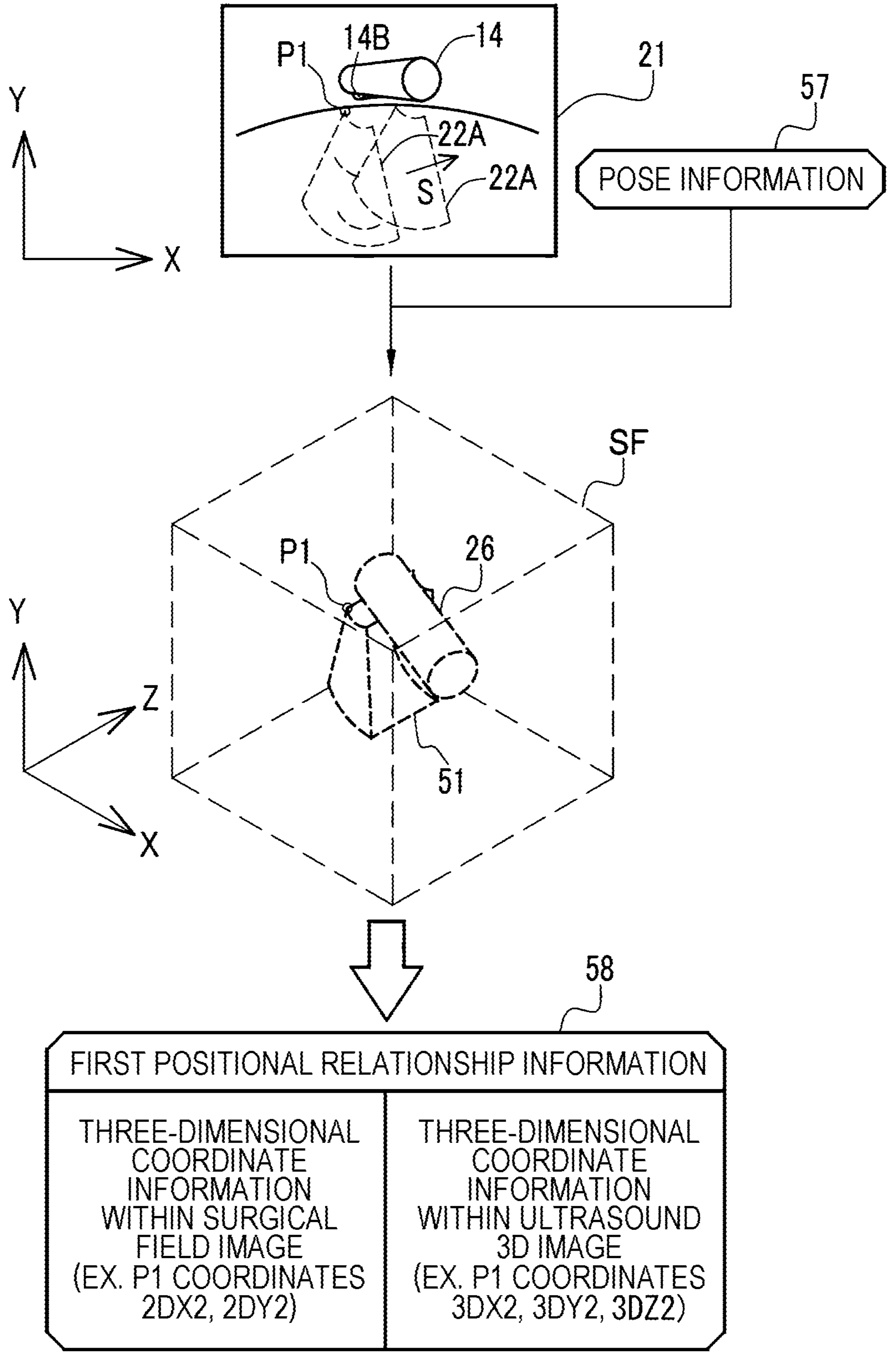
FIG. 14 is a diagram illustrating a second example of first positional relationship information.

Next, as illustrated in FIGS. 13 and 14, the processor 41 derives the first positional relationship information 58, which indicates the position and orientation of the ultrasound 3D image 51 within the surgical field image 21, on the basis of the pose information 57 that indicates the position and orientation, within the surgical field SF, of the ultrasound probe 14. The processing illustrated in FIGS. 13 and 14 corresponds to sub-step S1320 illustrated in FIG. 8. Note that in the surgical field image 21 illustrated in FIGS. 13 and 14, the ultrasound image 22A is indicated by dashed lines. This dashed-line ultrasound image 22A conveniently illustrates the position of the ultrasound image 22A estimated on the basis of the position of the ultrasonic transducer 14B within the surgical field image 21, and is not represented in the surgical field image 21 taken by the camera 13B of the endoscope 13.

FIG. 13 illustrates a case in which the position and orientation of the ultrasound probe 14 within the surgical field SF defined as the three-dimensional space are the same position and orientation as in FIG. 10. On the other hand, FIG. 14 illustrates a case in which the position and orientation of the ultrasound probe 14 within the surgical field SF are the same position and orientation as in FIG. 11. As illustrated in FIGS. 13 and 14, if the position and orientation of the ultrasound probe 14 within the surgical field SF can be ascertained from the pose information 57, the position and orientation of the ultrasonic transducer 14B within the surgical field SF can be ascertained. In addition, if the position and orientation of the ultrasonic transducer 14B can be ascertained, the position and orientation of the ultrasound 3D image 51 based on the ultrasound image group 22 can also be ascertained. For example, in the ultrasonic transducer 14B of the convex type, a fan-shaped ultrasound image 22A spreading out radially with the ultrasonic transducer 14B as a base point is acquired. When illustrated conceptually, the positional relationship within the surgical field SF is a positional relationship in which the position of the inner arc of the fan-shaped ultrasound image 22A and the ultrasonic transducer 14B are in proximity to one another. Since the ultrasound 3D image 51 is a three-dimensional image based on the ultrasound image group 22, the position and orientation of the ultrasound 3D image 51 within the surgical field SF can be ascertained.

Presupposing the above relationship, the processor 41 derives the first positional relationship information 58, which indicates the position and orientation of the ultrasound 3D image 51 within the surgical field image 21, on the basis of the pose information 57 that indicates the position and orientation of the ultrasound probe 14 within the surgical field SF. As illustrated in FIGS. 13 and 14, as one example, the first positional relationship information 58 is defined by two-dimensional coordinate information, that is, a position within the surgical field image 21, and three-dimensional coordinate information, that is, a position within the ultrasound 3D image 51. In the first positional relationship information 58 illustrated in FIGS. 13 and 14, a positional relationship between a point P1 within the surgical field image 21 and a point P1 within the ultrasound 3D image 51 is illustrated as an example.

Derivation of Second Positional Relationship Information

The processor 41 derives second positional relationship information 59, which indicates the positional relationship between a position within the ultrasound 3D image 51 and a position within the preoperative 3D image 34, by performing image analysis on the preoperative 3D image 34 and the ultrasound 3D image 51 that illustrate internal structures of the target area.

Figure 15:
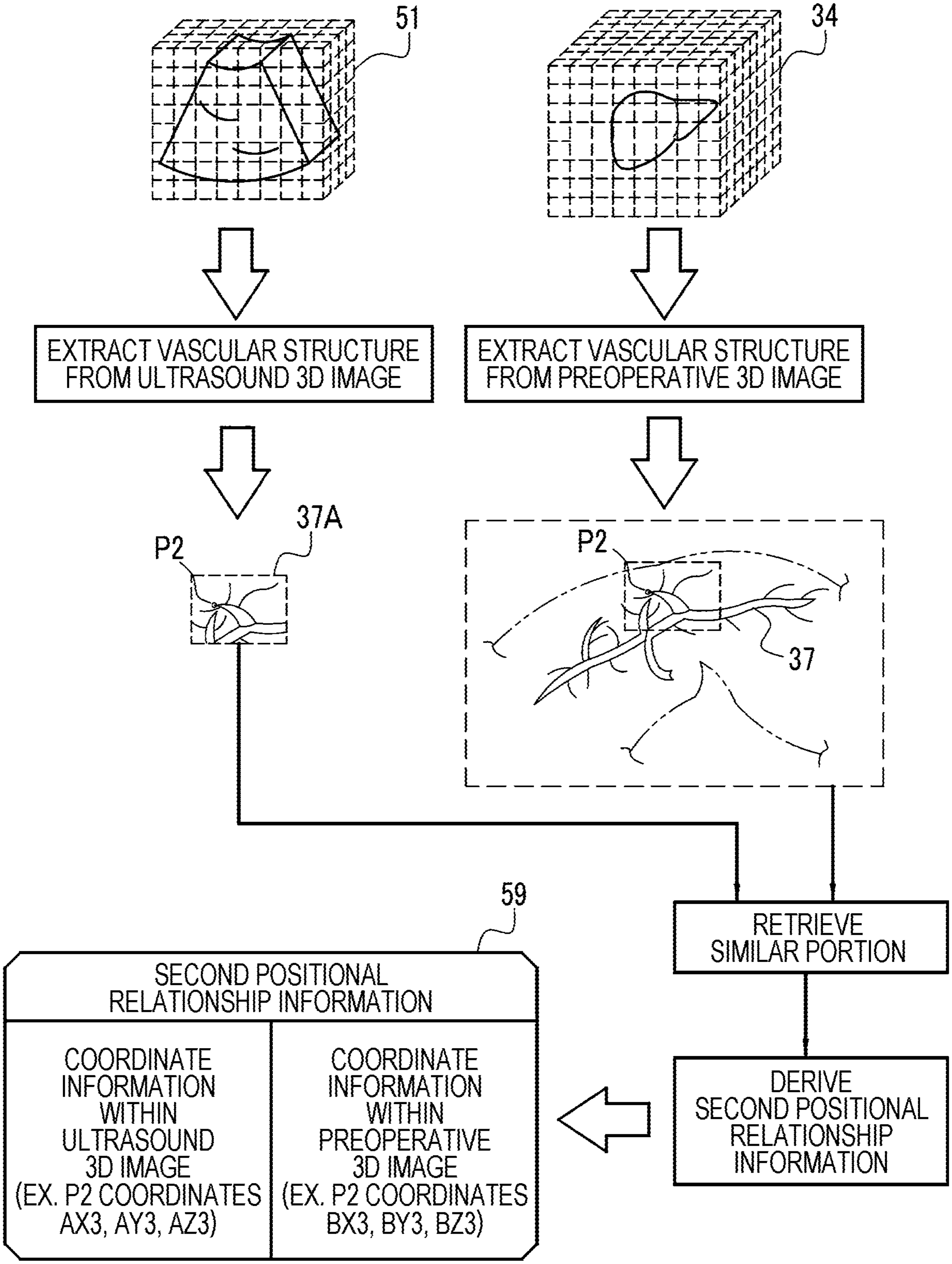
FIG. 15 is a diagram illustrating a procedure for deriving second positional relationship information.
Figure 16:
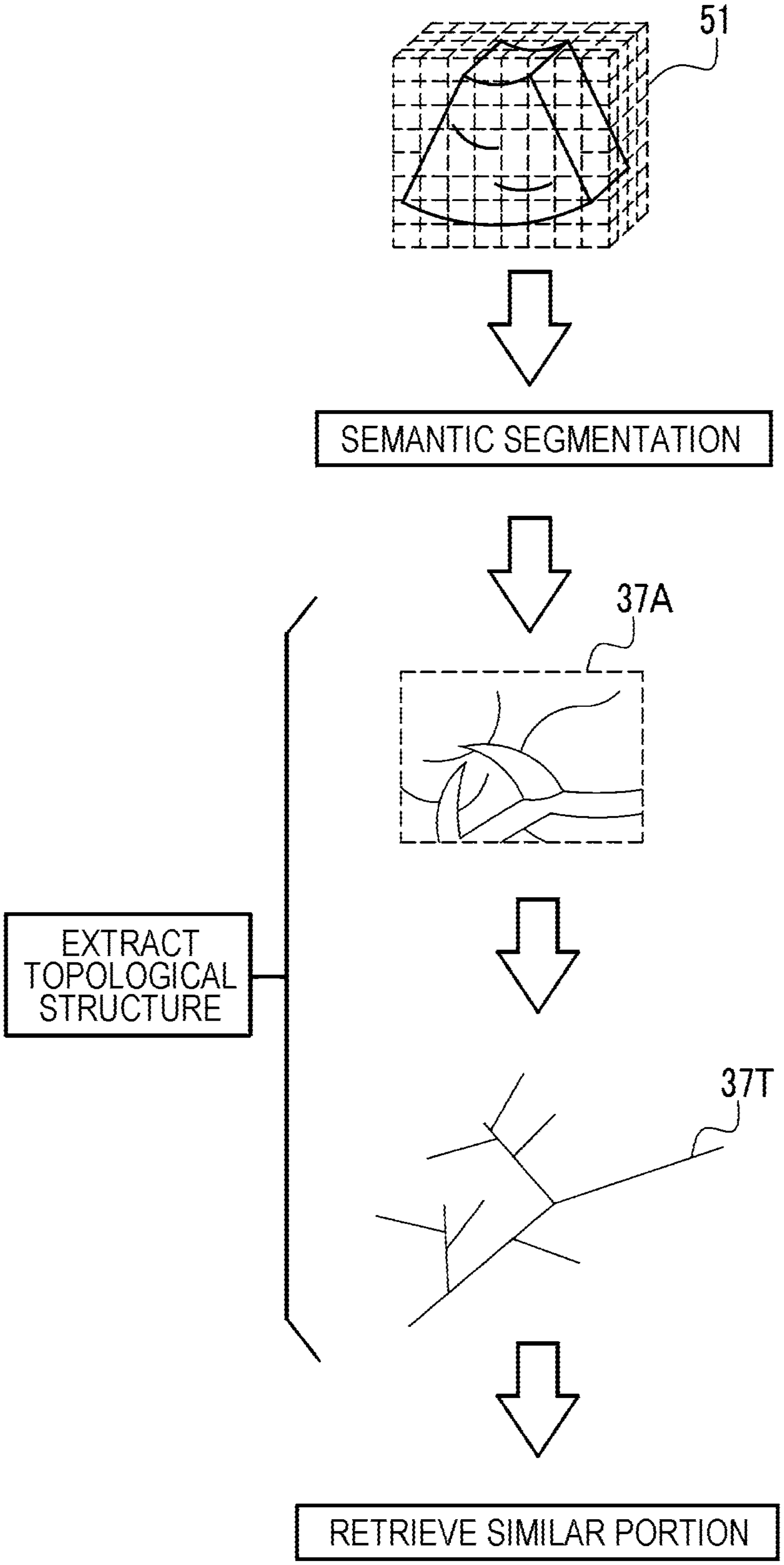
FIG. 16 is a diagram illustrating a procedure for morphological comparison of vascular structures.

FIGS. 15 and 16 is an explanatory diagram illustrating an example of processing to derive the second positional relationship information 59. In this example, the processor 41 derives the second positional relationship information 59 by comparing the morphologies of the vascular structure 37, which is an internal structure included commonly in both the ultrasound 3D image 51 and the preoperative 3D image 34. The processor 41 extracts the vascular structure 37 from each of the ultrasound 3D image 51 and the preoperative 3D image 34. As one example, the processor 41 derives the second positional relationship information 59 by comparing bifurcation points of blood vessels included in the vascular structure 37 in each of the ultrasound 3D image 51 and the preoperative 3D image 34 to one another. For convenience herein, the vascular structure 37 in the ultrasound 3D image 51 is denoted as 37A to distinguish between the vascular structure 37 in the ultrasound 3D image 51 and the vascular structure 37 in the preoperative 3D image 34. The image-taking range of the ultrasound 3D image 51 is narrow compared to the preoperative 3D image 34 acquired by a tomograph such as a CT apparatus. From the vascular structure 37A extracted from the preoperative 3D image 34, the processor 41 retrieves a portion that is similar to the vascular structure 37 extracted from the ultrasound 3D image 51.

As illustrated in FIG. 16, semantic segmentation using a machine learning model such as U-Net, which is one example of a convolutional neural network (CNN), is used as the method of extracting the vascular structure 37 from the ultrasound 3D image 51. U-Net is a typical machine learning model used in object recognition to identify different objects within an image. U-Net extracts image features by gradually reducing the image size of the input image while performing multiple types of filtering processing at each of the different image size levels. By extracting features at each of different image size levels, global features and local features of an image can be extracted. U-Net identifies different objects within an image on the basis of such features, and outputs an image in which the identified different objects are segmented.

The processor 41 performs semantic segmentation using U-Net on the ultrasound 3D image 51 and extracts the vascular structure 37A within the ultrasound 3D image 51. To compare the bifurcation points of the vascular structures 37 to one another, the processor 41 extracts a topological structure 37T, such as the number of bifurcation points included in the extracted vascular structure 37A. A topological structure refers to a structure of which the identity is maintained even when the vascular structure 37A is deformed while preserving continuity. The ultrasound 3D image 51 in this example is generated on the basis of the ultrasound image group 22 acquired in real time during specular surgery. Accordingly, the vascular structure 37 in the ultrasound 3D image 51 is deformed under the influence of the insufflation of the abdominal cavity by carbon dioxide gas, the breathing of the patient PT, and the like. By retrieving a similar portion of the vascular structure 37A on the basis of the topological structure 37T or other comparison of the bifurcation points of blood vessels to one another, the influence of real-time deformations can be mitigated to enable high-precision retrieval.

In FIG. 15, a positional relationship between coordinate information for each of a point P2 within the ultrasound 3D image 51 and a point P2 within the preoperative 3D image 34 is illustrated as one example of the second positional relationship information 59.

Generation of Composite Image

Figure 17:
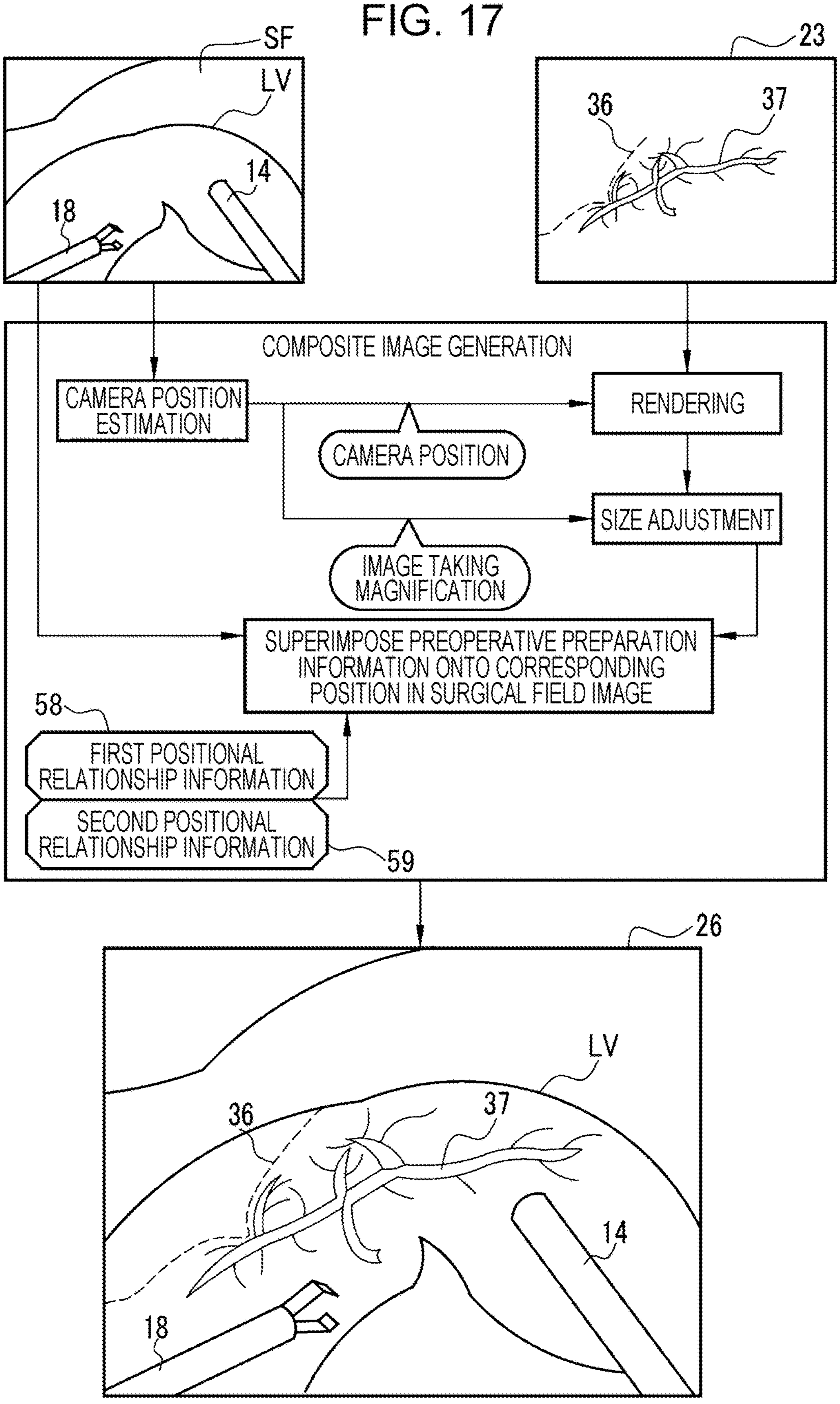
FIG. 17 is a diagram illustrating a procedure for generating a composite image.
Figure 18:
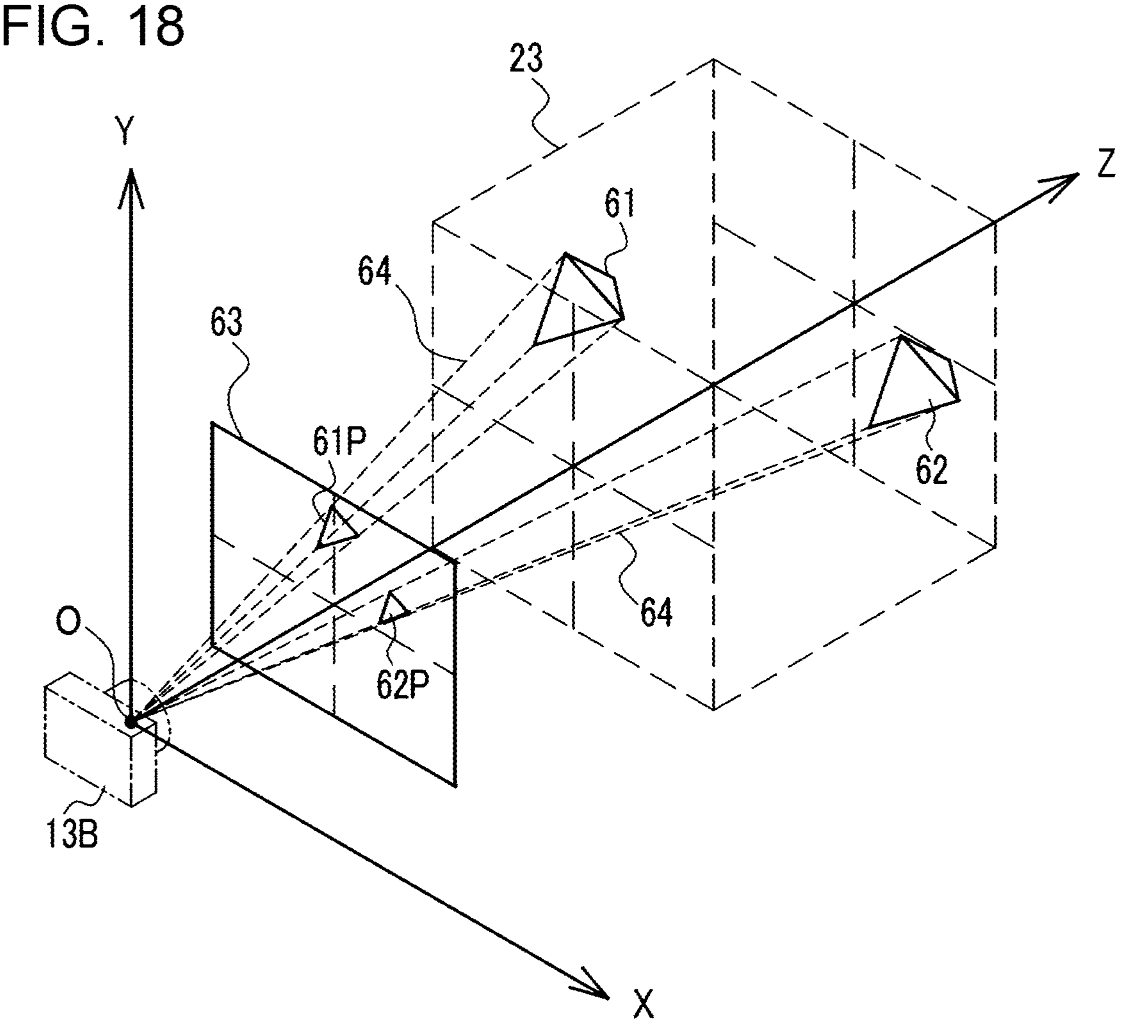
FIG. 18 is a diagram modeling the rendering of preoperative preparation information.
Figure 19:
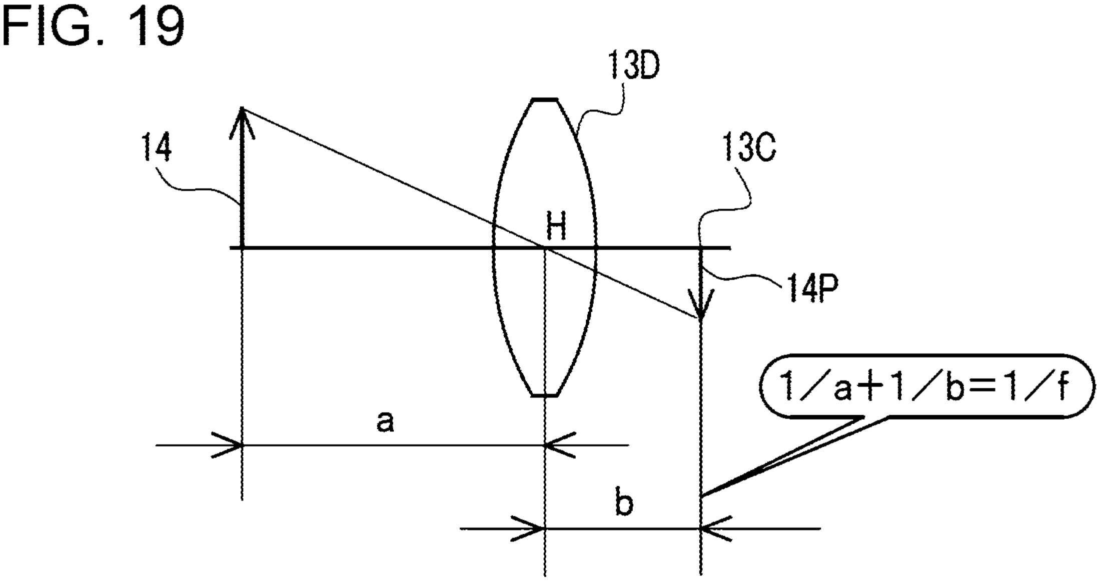
FIG. 19 is a diagram of the basic principle for estimating camera position from a surgical field image.

FIGS. 17 to 19 are diagrams for explaining a composite image generation process. The processor 41 generates the composite image 26 in which the preoperative preparation information 23 is superimposed onto the surgical field image 21. In the composite image 26, the processor 41 superimposes the preoperative preparation information 23 onto a corresponding position that corresponds to the target area within the surgical field image 21 on the basis of the first positional relationship information 58 and the second positional relationship information 59.

As illustrated in FIG. 17, when aligning the surgical field image 21 and the preoperative preparation information 23, the processor 41 first estimates the camera position of the camera 13B of the endoscope 13 that took the surgical field image 21. Since the preoperative preparation information 23 is information to be superimposed onto the surgical field image 21, the camera position is set as a viewpoint position in rendering the preoperative preparation information 23.

FIG. 18 is an explanatory diagram schematically illustrating the rendering of the preoperative preparation information 23. Since the preoperative preparation information 23 is generated on the basis of the preoperative 3D image 34, a position within the three-dimensional space is defined for each part of the preoperative preparation information 23. Sign 61 and sign 62 are three-dimensional regions that schematically illustrate parts of the preoperative preparation information 23, and correspond to parts of the vascular structure 37 included in the preoperative preparation information 23, for example.

Rendering is processing to project the preoperative preparation information 23 based on the preoperative 3D image 34 onto a two-dimensional projection plane 63 set virtually from the viewpoint position O. In other words, rendering is processing to simulate, through calculation, the image that would be formed on the image pick-up surface of the camera 13B in the case of placing the camera 13B at the viewpoint position O and taking an image of the preoperative preparation information 23. FIG. 18 is a modeling of the rendering, in which the projection plane 63 is disposed in front of the camera 13B, but the projection plane 63 corresponds to the image pick-up surface of the camera 13B.

Typical rendering techniques include perspective projection and parallel projection. Perspective projection can reproduce depth information in such a way that an object closer to the viewpoint position O is projected larger while an object farther away is projected smaller. With perspective projection, as illustrated in FIG. 18, projection lines 64 are drawn radially from a single viewpoint position O toward each of the regions 61 and 62 of the preoperative preparation information 23, and each of the regions 61 and 62 is projected at the position where the projection lines 64 extending from each of the regions 61 and 62 intersect with the projection plane 63.

In the example in FIG. 18, the region 61 is at a closer distance from the viewpoint position O than the region 62, and therefore a projected image 61P of the region 61 is larger than a projected image 62P of the region 62. In contrast, parallel projection is a method of projecting onto a projection plane using parallel projection lines extending in the normal direction with respect to the projection plane. With parallel projection, changes in size depending on the distance in the depth direction are not reproduced. In the case of this example, the taking of an image by the camera 13B is simulated, and therefore perspective projection is used. Also, pixel values in the projection plane 63 are obtained by a ray casting technique for adding up a plurality of voxel data 34A intersecting the projection lines 64 in the preoperative preparation information 23, for example.

FIG. 19 is an explanatory diagram for explaining the principle for obtaining the camera position to be set as the viewpoint position O from the surgical field image 21. The processor 41 estimates the camera position of the camera 13B of the endoscope 13 on the basis of the size of the ultrasound probe 14 appearing in the surgical field image 21. When an image of the ultrasound probe 14 within the surgical field SF is taken by the camera 13B, an image 14P of the ultrasound probe 14 is formed on the image pick-up surface 13C of the camera 13B by imaging optics 13D of the camera 13B. The focal length f of the imaging optics 13D and the distance b from the principal point H of the imaging optics 13D to the image pick-up surface 13C when in focus are known and can be acquired from the camera 13B. Accordingly, provided that a is the subject distance, the size of the image 14P within the surgical field image 21 is determined on the basis of the imaging formula, which is defined as $1/a+1/b=1/f$. Since the size of the ultrasound probe 14 is also known, if the size of the image 14P is known, the unknown subject distance a can be estimated on the basis of the imaging formula.

Returning to FIG. 17, the processor 41 sets the camera position estimated from the surgical field image 21 as the viewpoint position O and renders the preoperative preparation information 23. Additionally, the processor 41 adjusts the size of the preoperative preparation information 23 converted to a two-dimensional image by the rendering on the basis of the image-taking magnification, which is determined from the focal length f, and the estimated subject distance a. Through such size adjustment, the preoperative preparation information 23 can be fitted to the size of the surgical field image 21.

The processor 41 superimposes the rendered and size-adjusted preoperative preparation information 23 onto the corresponding position in the surgical field image 21, on the basis of the first positional relationship information 58 and the second positional relationship information 59. Specifically, a composite image 26 is generated in a state such that the excision line 36 and the vascular structure 37 of the liver LV included in the preoperative preparation information 23 are aligned in position and orientation with the liver LV in the surgical field image 21. The processor 41 outputs the generated composite image 26 to the display 16 and controls the displaying of the composite image 26.

Figure 20:
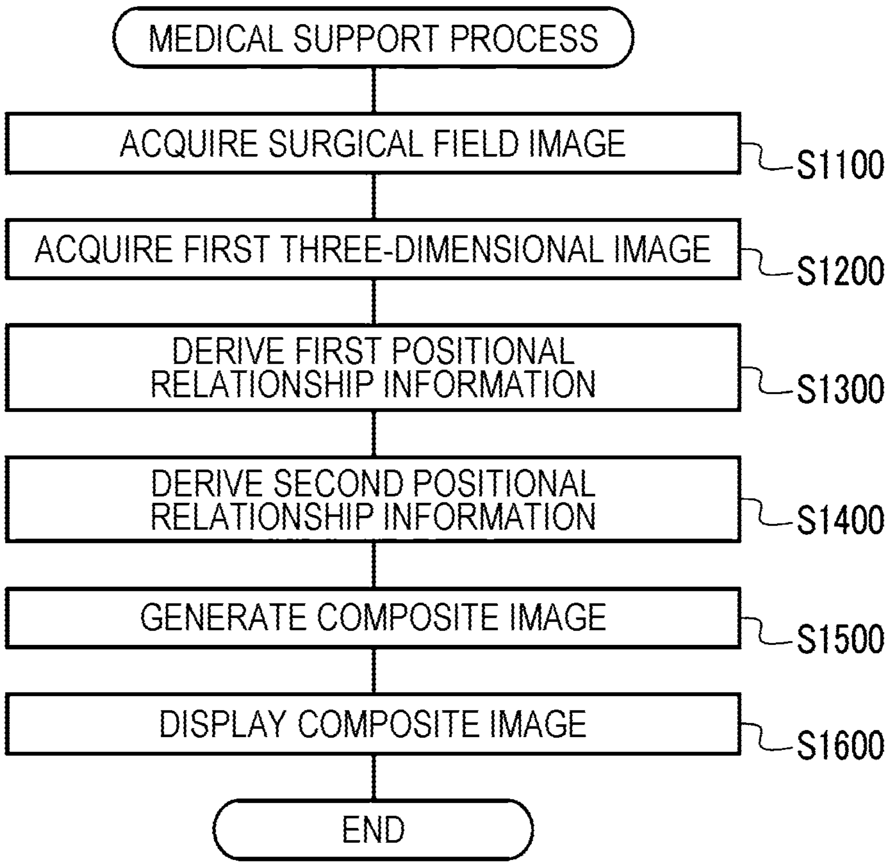
FIG. 20 is a flowchart illustrating an overall procedure of a medical support process.
Figure 21:
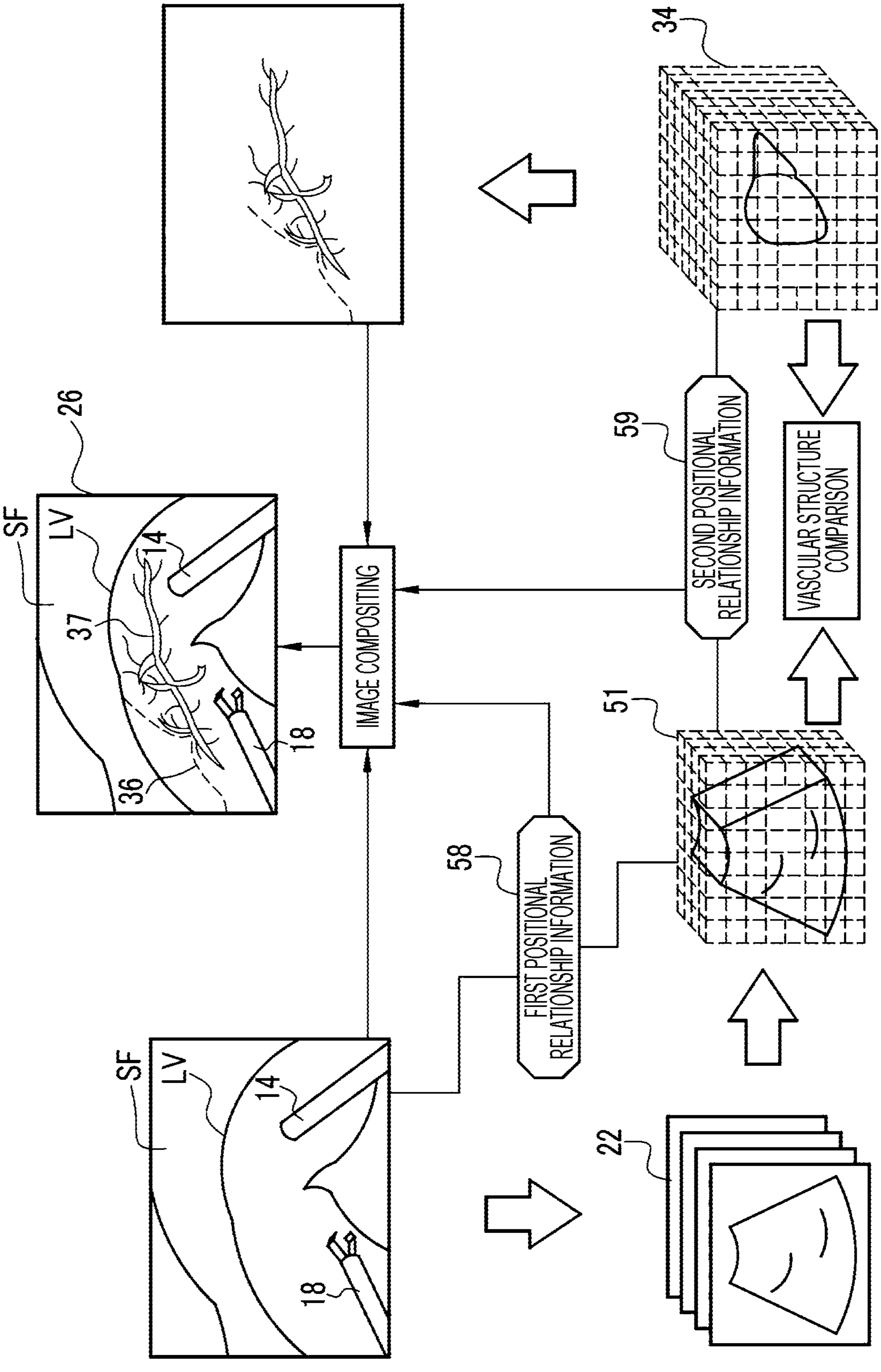
FIG. 21 is a conceptual diagram summarizing a medical support process.

The action and effects of the above configuration will be described using FIGS. 20 and 21. FIG. 20 is a flowchart of the medical support process in this example using the medical support apparatus 11, and FIG. 21 is an explanatory diagram that schematically illustrates a summary of the medical support process in this example.

The medical support process in this example is executed during specular surgery. In performing the medical support process, the preoperative preparation information 23 is created prior to surgery. As one example, the preoperative preparation information 23 is created according to the procedure explained using FIGS. 3 and 4. After the preoperative preparation information 23 is prepared, specular surgery like that illustrated in FIGS. 1 and 2 is performed.

In step S1100, the processor 41 acquires the surgical field image 21 from the camera 13B of the endoscope 13 and outputs the surgical field image 21 to the display 16. Accordingly, a visual field of the inside of the body is provided to the medical staff ST. While observing the surgical field image 21 on the display 16, the medical staff ST use the ultrasound probe 14 to scan the surface of the liver LV, which is the target area in this example, as illustrated in FIG. 6.

In step S1200, the processor 41 acquires the ultrasound image group 22 (corresponding to the first three-dimensional image) taken by the ultrasound probe 14. The processor 41 generates the ultrasound 3D image 51 on the basis of the ultrasound image group 22 according to the procedure illustrated in FIG. 7 as one example.

In step S1300, first, the processor 41 estimates the position and orientation of the ultrasound probe 14 within the surgical field SF by performing image analysis on the surgical field image 21 according to the procedure illustrated in FIGS. 8 to 12 as one example, and derives the pose information 57. The processor 41 then derives the first positional relationship information 58 indicating the position and orientation of the ultrasound 3D image 51 within the surgical field image 21 on the basis of the pose information 57 according to the procedure illustrated in FIGS. 13 and 14 as one example.

In step S1400, the processor 41 derives the second positional relationship information 59, which indicates the positional relationship between a position within the ultrasound 3D image 51 and a position within the preoperative 3D image 34, by performing image analysis on the ultrasound 3D image 51 and the preoperative 3D image 34 according to the procedure illustrated in FIG. 15 as one example.

In step S1500, the processor 41 superimposes the preoperative preparation information 23 related to the liver LV onto the corresponding position that corresponds to the liver LV, which is the target area in this example, within the surgical field image 21, on the basis of the first positional relationship information 58 and the second positional relationship information 59, according to the procedure illustrated in FIG. 17 as one example. With this arrangement, the composite image 26 is generated.

In step S1600, the processor 41 displays the composite image 26 on the display 16.

As described above, according to the medical support apparatus 11 as in the technology of the present disclosure, the preoperative preparation information 23 can be superimposed onto an appropriate position within the surgical field image 21, without using an external sensor. That is, as illustrated in FIG. 21, the processor 41 of the medical support apparatus 11 in this example uses the ultrasound 3D image 51, which is based on the ultrasound image group 22 taken by the ultrasound probe 14 inserted into the surgical field SF, to align the surgical field image 21 and the preoperative preparation information 23. Additionally, the processor 41 derives the first positional relationship information 58 that is the positional relationship between the surgical field image 21, which includes the ultrasound probe 14, and the ultrasound 3D image 51. Furthermore, by comparing the morphologies of the vascular structure 37, the processor 41 derives the first positional relationship information 58 that indicates the positional relationship between the ultrasound 3D image 51 and the preoperative 3D image 34. The processor 41 derives such first positional relationship information 58 and second positional relationship information 59 through image analysis. This ties the positional relationship between the surgical field image 21 and the preoperative 3D image 34, using the ultrasound 3D image 51 as a base point. Accordingly, the medical support apparatus 11 according to the present disclosure can superimpose the preoperative preparation information 23 onto an appropriate position within the surgical field image 21, without using an external sensor.

Also, displaying the excision line 36 and the vascular structure 37 at appropriate positions within the surgical field image 21 makes it possible to carry out treatment, such as excising a portion of the liver LV, while avoiding the vascular structure 37.

Also, in this example, the optically detectable marker 56 is provided on the outer circumferential surface of the ultrasound probe 14, and when deriving the pose information 57, the processor 41 estimates the position and orientation of the ultrasound probe 14 by detecting the marker 56 from the surgical field image 21. Providing the marker 56 to be used for recognition of position and orientation allows for easier recognition of position and orientation compared to the case with no marker 56.

As for the form of the marker 56, in this example, a lattice marker 56 formed by lines in the axial direction and lines in the circumferential direction of the ultrasound probe 14 is used. Accordingly, the position and orientation of the ultrasound probe 14 is estimated more easily compared to the case where, for example, a single figure such as a simple polygon or circle is provided as a marker.

Obviously, the form of the marker 56 need not be a lattice marker as in this example, and may also be a single figure such as a simple polygon or circle, or a combination of a plurality of such figures. Furthermore, the form of the marker 56 may also be a dot pattern of equally spaced dots arrayed in a matrix.

The estimation of the position and orientation of the ultrasound probe 14 within the surgical field SF may also be performed without using a marker. A conceivable method for estimating the position and orientation of the ultrasound probe 14 without using a marker may be, for example, a method of using a machine learning model to estimate the position and orientation from shape information about the ultrasound probe 14. In this case, combinations of a plurality of surgical field images 21 with various changes in the position and orientation of the ultrasound probe 14 and pose information 57 serving as ground truth data for each are prepared as teaching data. This teaching data is used to train a machine learning model and thereby generate a trained model that outputs pose information 57 in response to an inputted surgical field image 21.

Also, in the above example, the processor 41 derives the second positional relationship information 59 by comparing the morphologies of an internal structure of the target area in each of the ultrasound 3D image 51 and the preoperative 3D image 34. Since the morphologies of an internal structure are compared, the second positional relationship information 59 is derived more easily compared to the case of not performing a morphology comparison of an internal structure. Also, in the above example, the vascular structure 37 is given as one example of an internal structure, but the internal structure need not be the vascular structure 37 insofar as the internal structure is a characteristic internal structure suitable for morphology comparison.

Also, the method for morphology comparison of an internal structure may be a rules-based method such as pattern matching, or a method that uses a machine learning model.

In the above example, the processor 41 derives the second positional relationship information 59 by comparing bifurcation points of blood vessels included in the vascular structure 37 in each of the ultrasound 3D image 51 and the preoperative 3D image 34 to one another. Since the bifurcation points of blood vessels in the vascular structure 37 are characteristic information, the degree of coincidence between vascular structures 37 is determined more easily compared to the case of not comparing bifurcation points.

Superimposing of Information Acquired During Surgery

Also, the above example describes an example of superimposing the preoperative preparation information 23 within the surgical field image 21, but in addition to the preoperative preparation information 23, information acquired during surgery, such as the ultrasound image 22A, may also be superimposed onto the surgical field image 21.

Timing of Superimposing

The timing of the superimposing of the preoperative preparation information 23, that is, the timing at which to switch from the surgical field image 21 to the composite image 26, may be the timing at which the scanning by the ultrasound probe 14 is performed. For example, the processor 41 monitors the movement of the ultrasound probe 14 on the basis of the surgical field image 21, and when the amount of movement of the ultrasound probe 14 exceeds a preset threshold value, the processor 41 switches from the surgical field image 21 to the composite image 26. Note that the switching condition is not particular limited to the above, and the medical support apparatus 11 may also switch between the surgical field image 21 and the composite image 26 when a switching instruction inputted via the reception device 42 is obtained, or the medical support apparatus 11 may have a function for displaying the composite image 26 only.

Adjustment of Display Position of Preoperative Preparation Information

When superimposing the preoperative preparation information 23, the display position of the preoperative preparation information 23 may also be adjustable in consideration of cases in which information to be displayed in the background is present. Manual adjustment may also be possible, or the display position may be adjusted to not overlap with a specific region within the surgical field image 21 when the specific region is recognized.

Correction of Surgical Field Image According to Optical Characteristics of Camera The surgical field image 21 may also be corrected according to the optical characteristics of the camera 13B. In particular, if the imaging optics 13D of the camera 13B have a large amount of distortion, the surgical field image 21 will be distorted, and the liver LV or the like will be in a deformed state. If the liver LV is deformed, the alignment precision will be impaired. Distortion can be broadly classified into barrel distortion and pincushion distortion, and it is preferable to correct the surgical field image 21 according to the optical characteristics of the imaging optics 13D.

Modification 1: Apply Deformation of Internal Structure

The processor 41 may also acquire deformation information indicating how the internal structure in the ultrasound 3D image 51 is deformed with respect to the internal structure in the preoperative 3D image 34 prepared in advance, deform the preoperative preparation information 23 on the basis of the acquired deformation information, and generate the composite image 26 with the deformed preoperative preparation information 23 superimposed onto the surgical field image 21.

Figure 22:
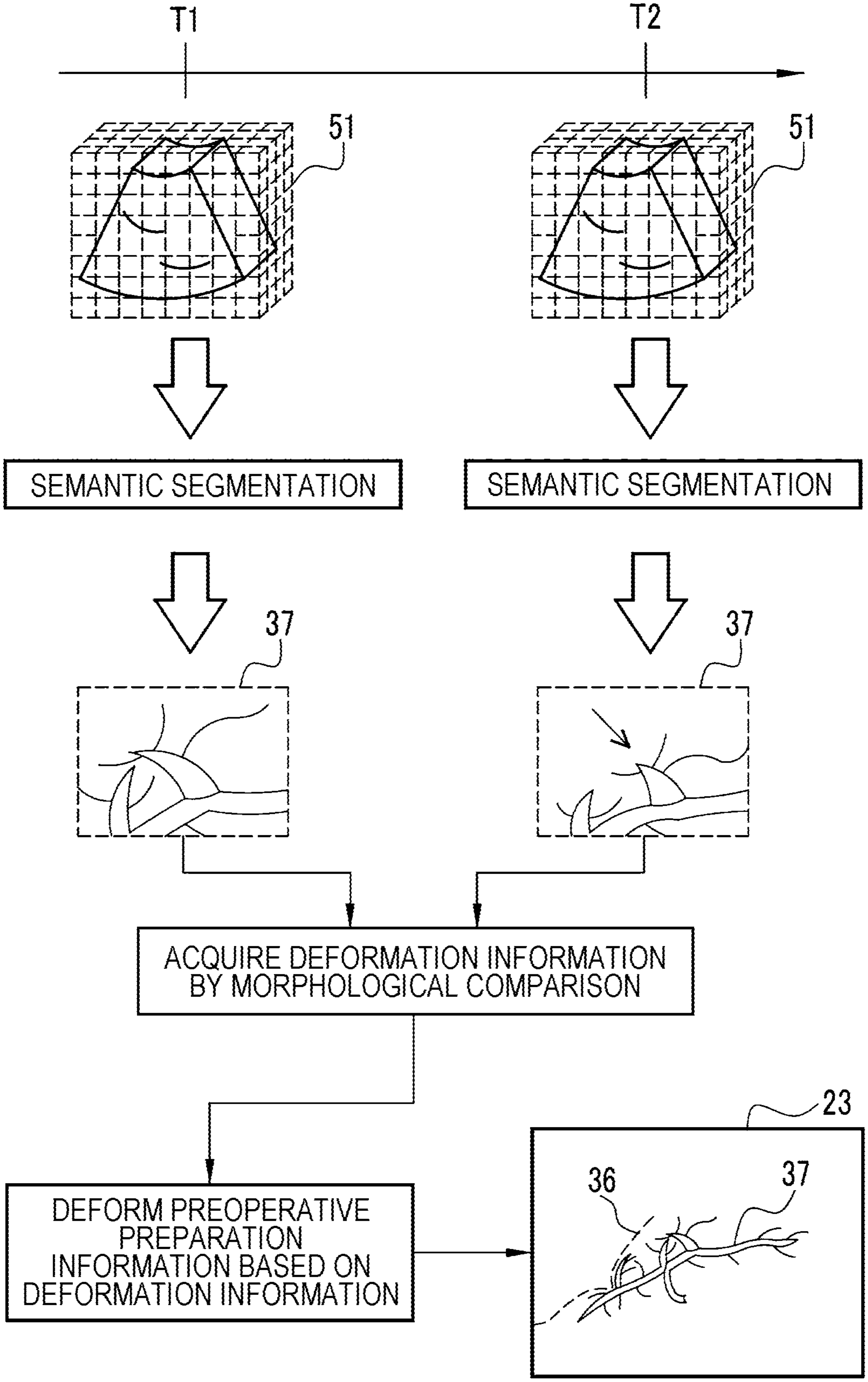
FIG. 22 is a diagram in which target area deformation information is reflected in preoperative preparation information.
Figure 23:
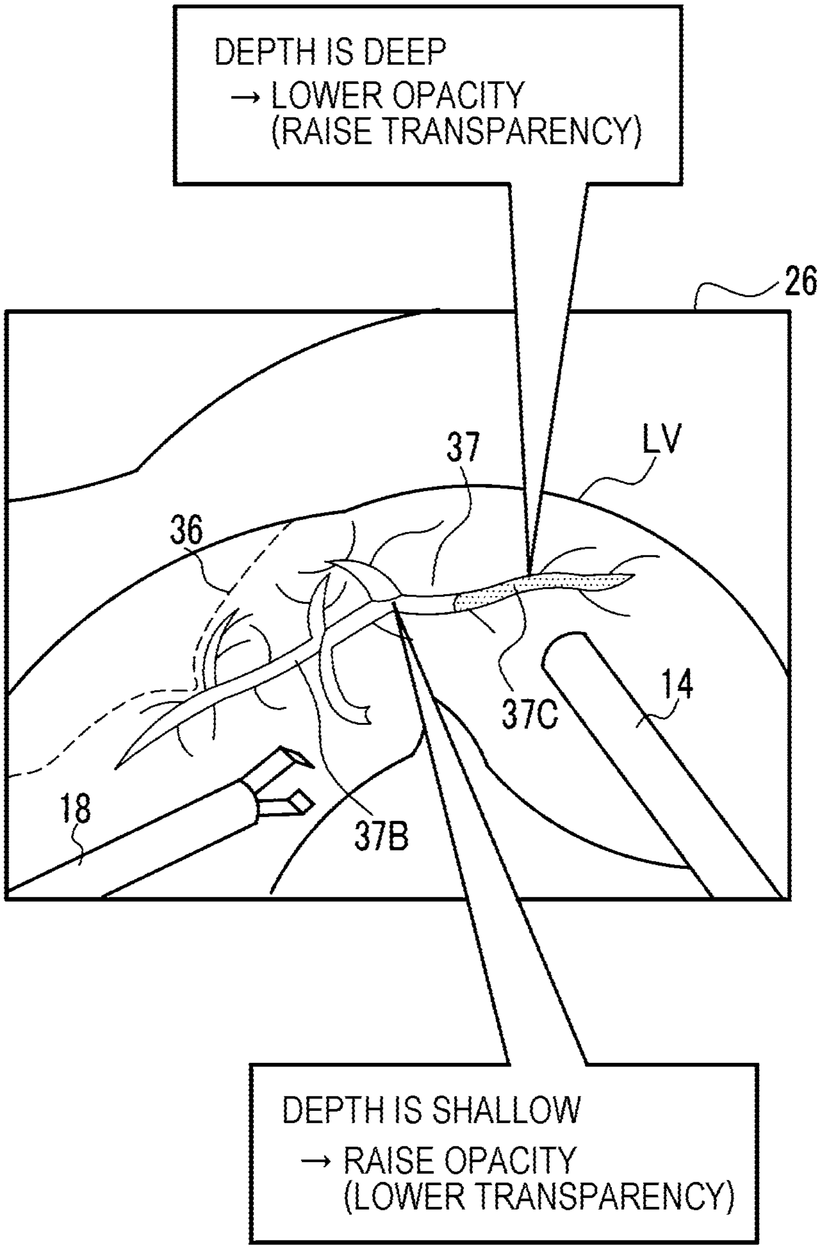
FIG. 23 is a diagram in which the display appearance of information that differs by depth is changed.

As illustrated in FIG. 22, the processor 41 acquires the ultrasound 3D image 51 at a time different from during surgery. In the example in FIG. 22, the ultrasound 3D image 51 is acquired at each of time T1 and time T2. The processor 41 extracts the vascular structure 37 from the ultrasound 3D image 51 at each of times T1 and T2. The processor 41 acquires deformation information through morphology comparison of the vascular structure 37. In FIG. 22, the vascular structure 37 at time T2 is illustrated as being crushed in the direction indicated by the arrow as compared to the state at time T1. The processor 41 deforms the preoperative preparation information 23 on the basis of the deformation information acquired in this way. As described above, in specular surgery, the target area such as the liver LV is also deformed under the influence of insufflation, breathing, and the like. As the target area is deformed, the internal structure, namely the vascular structure 37, is also deformed. By deforming the preoperative preparation information 23 according to the deformation state of the vascular structure 37, the preoperative preparation information 23 can be superimposed with an appropriate position, orientation, and size according to the current state of the target area. With this arrangement, the form of the preoperative preparation information 23 can be made to follow the deformation of the target area in real time.

The target area is particularly susceptible to the influence of insufflation and the like when the target area is soft tissue such as the liver LV and the lung LG described later (see FIG. 31). Accordingly, when the target area is soft tissue, causing the form of the preoperative preparation information 23 to follow the deformation of the target area has a greater effect compared to when the target area is not readily deformed.

Also, the ultrasound 3D image 51 has an extremely narrow image-taking range compared to the preoperative 3D image 34. Accordingly, the deformation information that can be acquired on the basis of the ultrasound 3D image 51 is extremely narrow local deformation information on the preoperative 3D image 34. In this case, the processor 41 may also predict deformation outside the image-taking range of the ultrasound 3D image 51 by extrapolation on the basis of the local deformation information acquired from the ultrasound 3D image 51.

Second Embodiment

As described in the first embodiment, since the preoperative preparation information 23 is information based on the preoperative 3D image 34, a plurality of pieces of preoperative preparation information 23 at different depths in the depth direction proceeding from the surface layer to the deep layers of the target area in the preoperative 3D image 34 is included. This makes it possible to provide more detailed preoperative preparation information 23 in accordance with the depth of the target area.

The second embodiment illustrated in FIGS. 23 to 27 is an example in which, when superimposing a plurality of pieces of preoperative preparation information 23 at different depths onto the surgical field image 21, the processor 41 changes the display appearance of the plurality of pieces of preoperative preparation information 23 in the composite image 26 according to the depth. Herein, display appearance is a concept that includes any of color, luminance, opacity, line thickness, and the like. In the composite image 26 illustrated in FIG. 23, the opacity is changed for a plurality of regions 37B and 37C at different depths of the vascular structure 37. The region 37B is at a shallow depth and for this reason the opacity is raised. That is, the transparency is lowered. On the other hand, the region 37C is at a deep depth and for this reason the opacity is lowered. That is, the transparency is raised. In this way, changing the display appearance of information at different depths can prevent confusion of a plurality of information at different depths.

Figure 24:
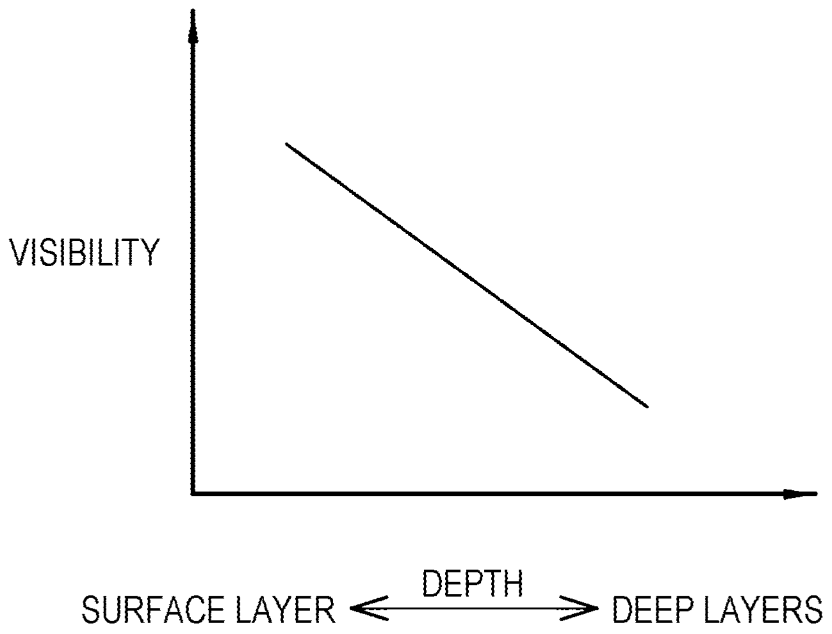
FIG. 24 is a diagram of an example in which visibility is increased for shallower depths.

Also, as illustrated in FIG. 24, when changing the display appearance, the processor 41 may also raise the visibility of the preoperative preparation information 23 nearer the surface layer than deep layers. Conceivable methods of raising the visibility include methods such as making the color relatively easy to distinguish from the color of the background, increasing the luminance, making lines relatively thicker, and raising the opacity relatively for regions nearer the surface layer as compared to deep layers.

As illustrated in FIG. 22, for the plurality of regions 37B and 37C in the vascular structure 37, the visibility of the region 37B nearer the surface layer may be raised higher than that of the region 37C nearer the surface layer. As another example, in the case where the preoperative preparation information 23 nearer the surface layer is taken to be the excision line 36 of the liver LV and the preoperative preparation information 23 nearer the deep layers is taken to be the vascular structure 37 internal to the liver LV, the visibility of the excision line 36 nearer the surface layer may be raised.

By raising the visibility nearer the surface layer higher than the deep layers, the medical staff ST can intuitively understand the positional relationship of a plurality of pieces of preoperative preparation information 23. Note that when displaying only the preoperative preparation information 23 near the surface layer, the visibility of the preoperative preparation information 23 at the surface layer may also be raised higher than surrounding regions.

Figure 25:
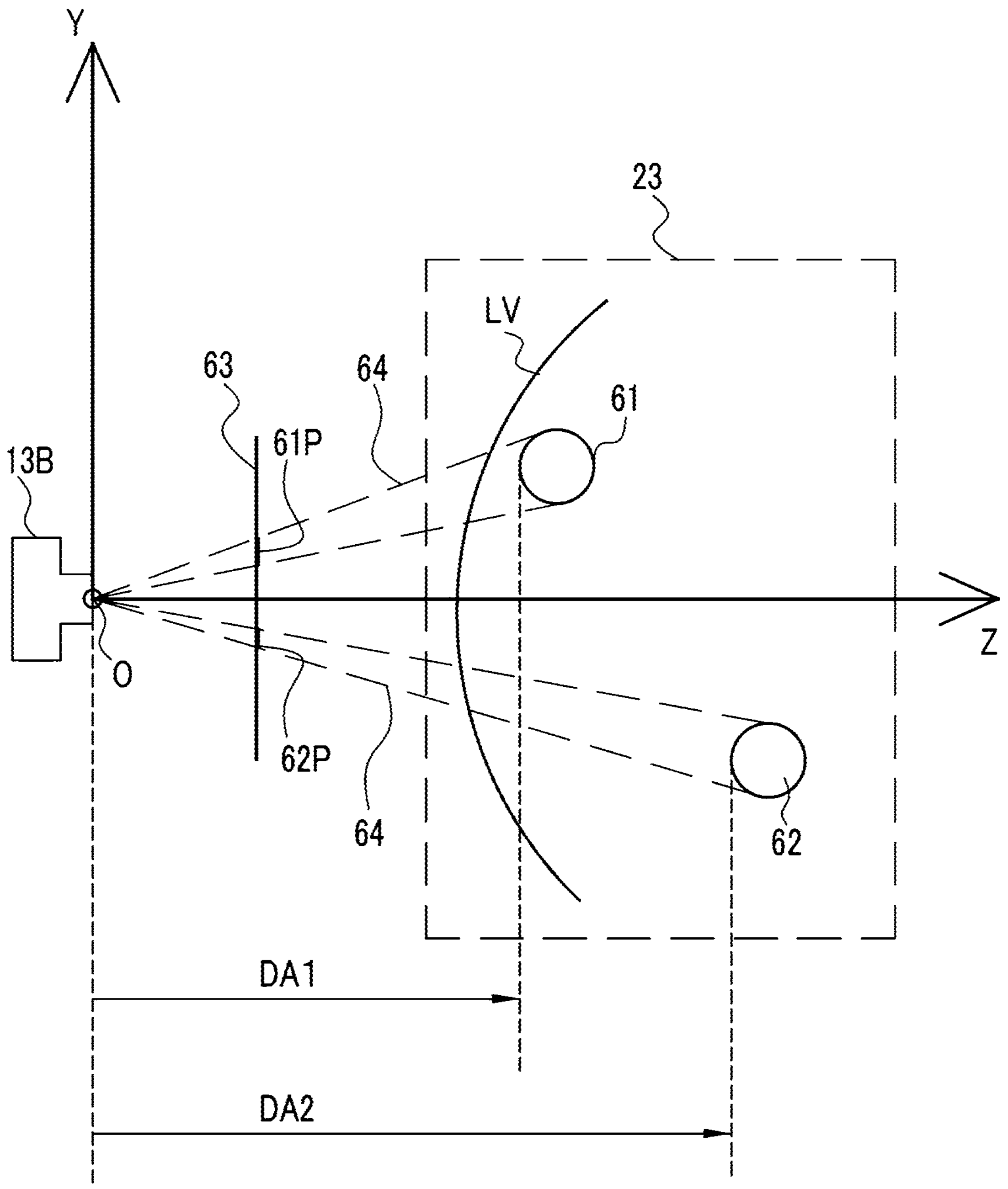
FIG. 25 is a diagram of a case of taking a viewpoint position O as a depth reference position.
Figure 26:
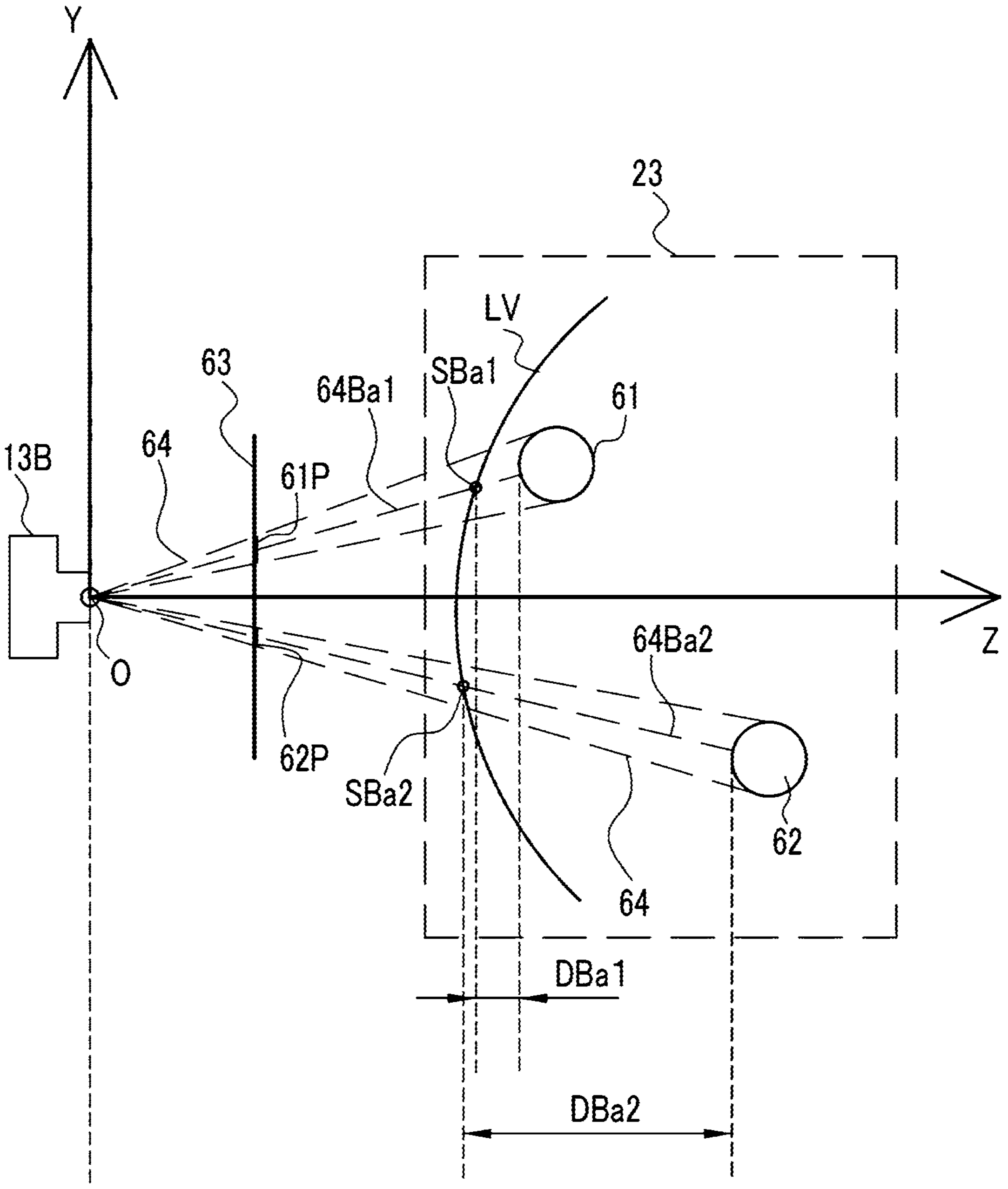
FIG. 26 is a diagram illustrating a first example of taking a surface position of a target area as a depth reference position.
Figure 27:
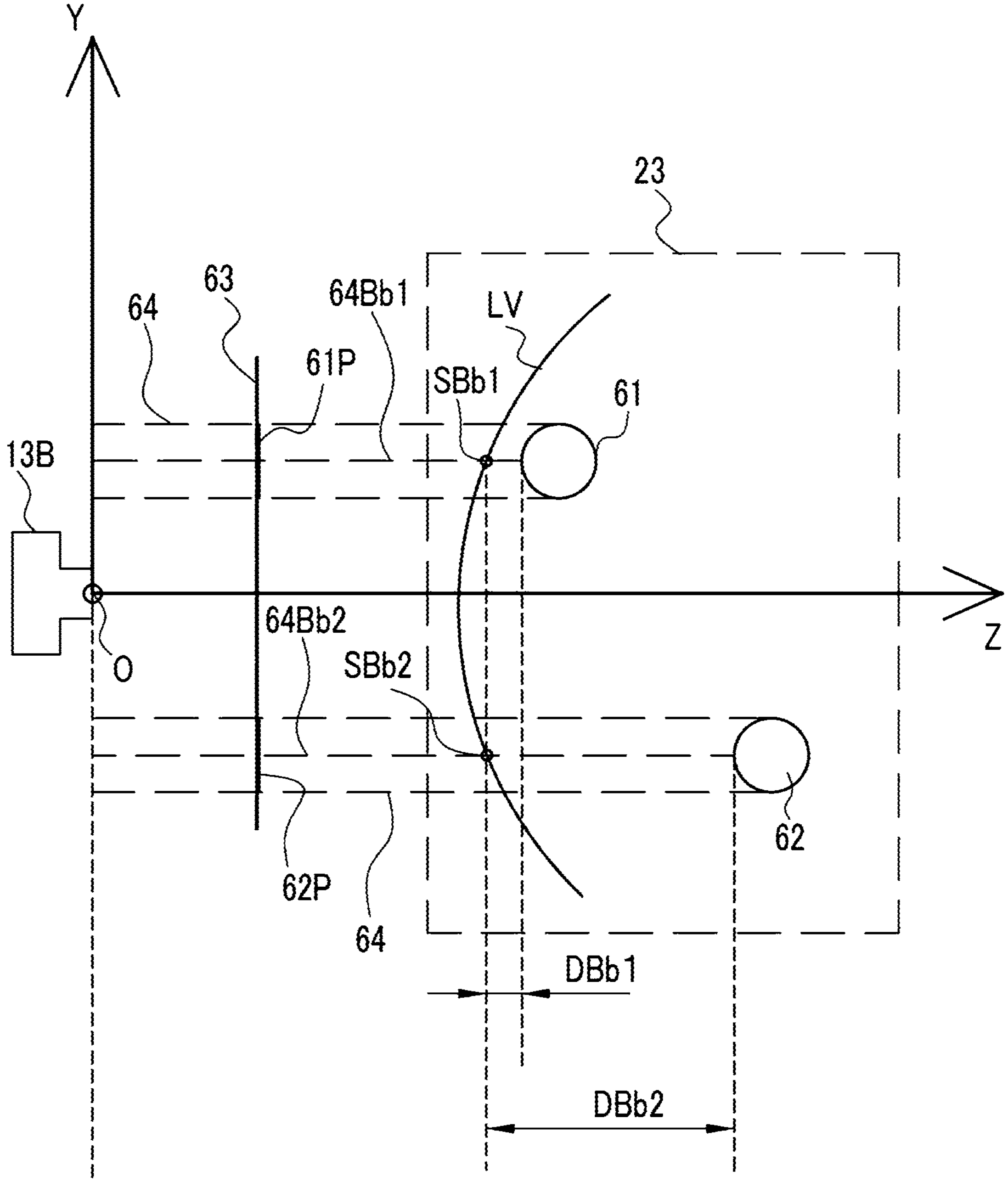
Figure 28:
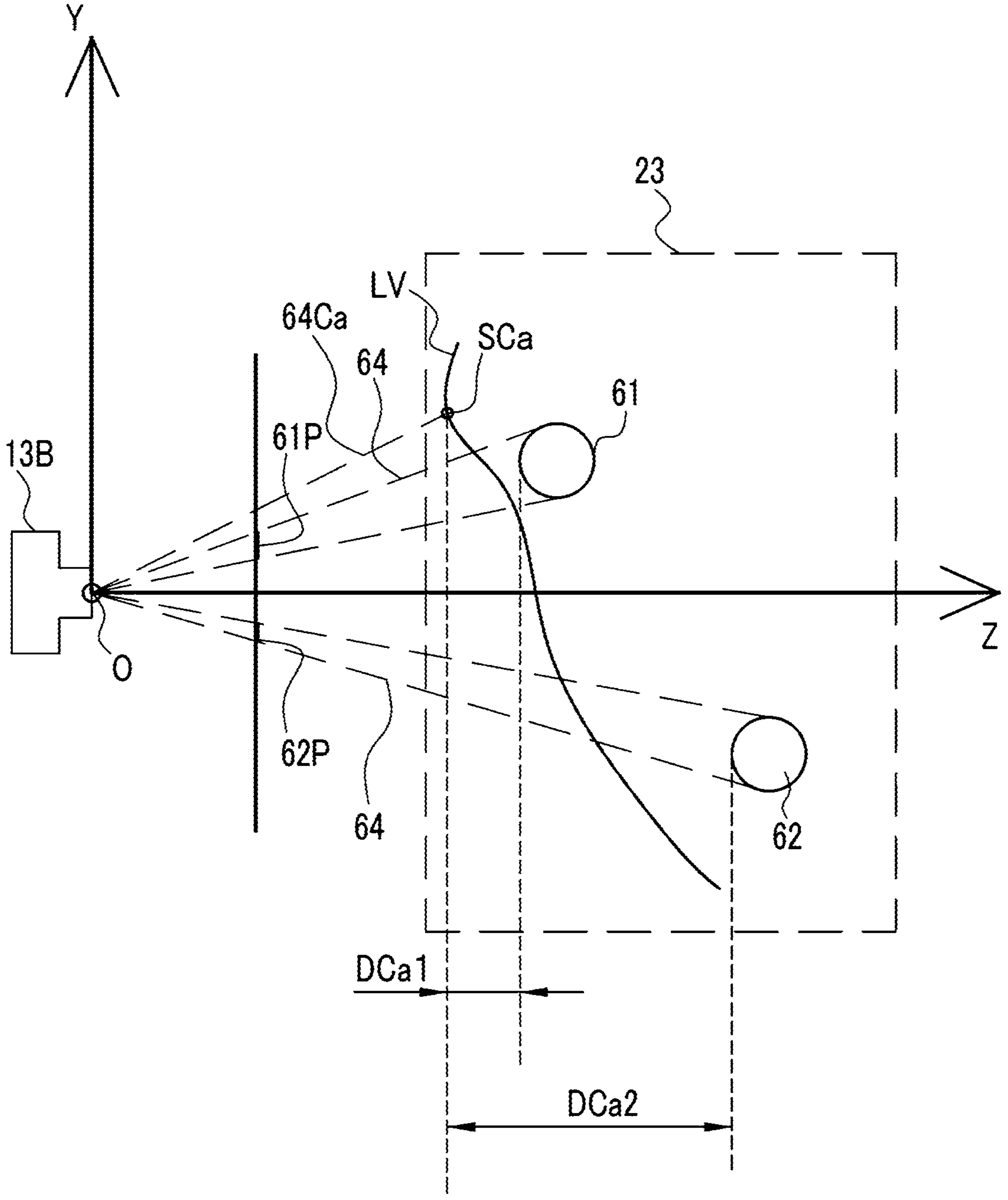
FIG. 28 is a diagram illustrating a second example of taking a surface position of a target area as a depth reference position.
Figure 29:
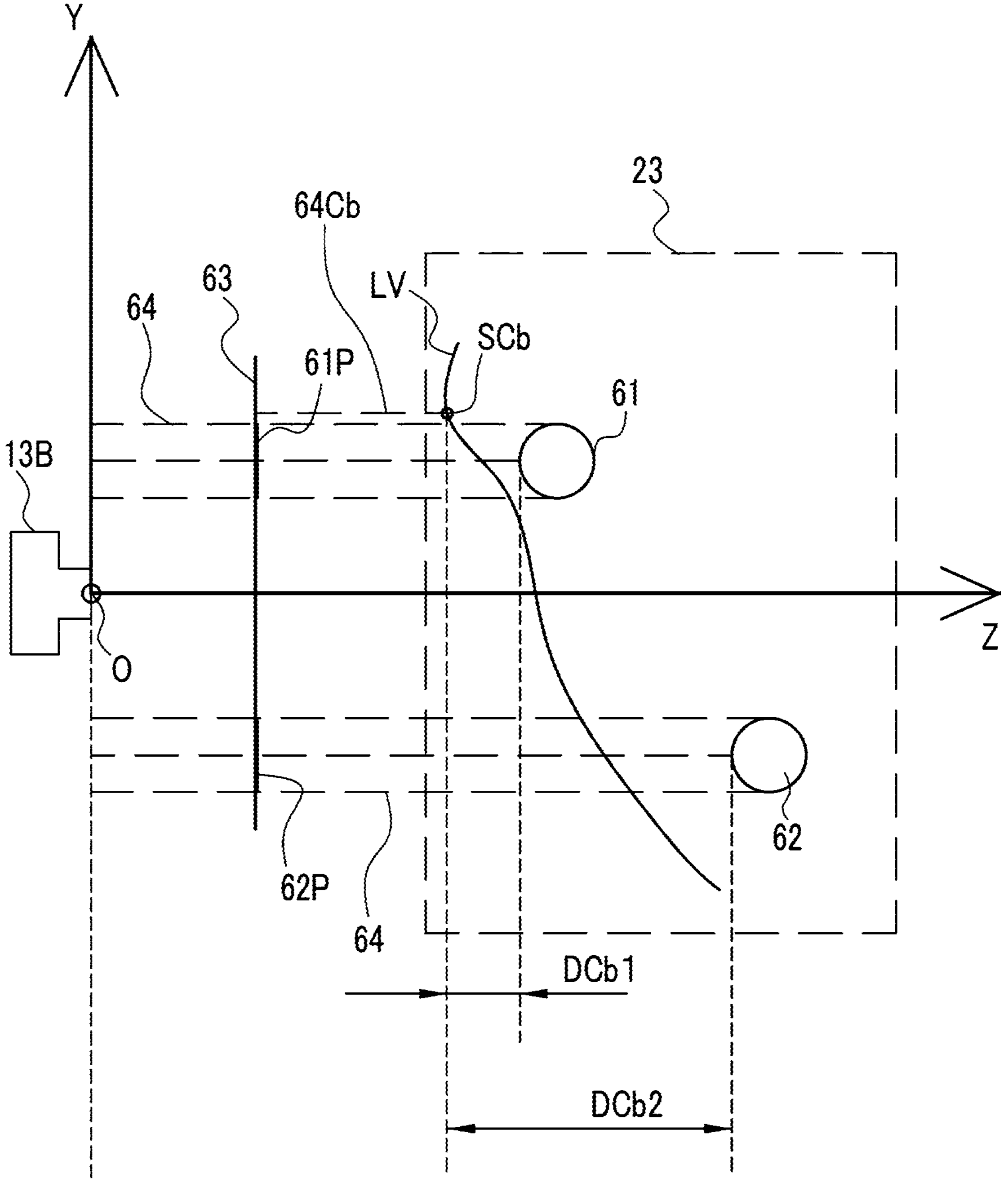

Also, as illustrated in FIGS. 25 to 30, a variety of depths are possible, depending on how a reference position is defined and the like. FIGS. 25 to 30 are schematic diagrams modeling rendering in a manner similar to FIG. 18. Of these, FIGS. 25, 26, 28, and 30 are each a modeling of perspective projection in a manner similar to FIG. 18, while FIGS. 27 and 29 are each a modeling of parallel projection.

In the examples illustrated in FIGS. 25 to 29, the depth direction is the direction along the image-taking optical axis (the Z axis in FIGS. 25 to 29) of the camera 13B that takes the surgical field image 21. The camera position of the camera 13B in the surgical field image 21 coincides with the viewpoint of the medical staff ST observing the surgical field image 21. Accordingly, by defining the depth direction to be the direction along the image-taking optical axis, the near side in the viewing direction of the medical staff ST corresponds to the surface layer side, and the far side corresponds to the deep layer side. Accordingly, there is less discomfort for the medical staff ST in understanding the positional relationship.

Also, in FIGS. 25 to 29, a depth reference position in the depth direction is different. In FIG. 25, the depth reference position is the viewpoint position O of the camera 13B. When there are the regions 61 and 62 at different depths within the liver LV which is the target area, the depth of each of the regions 61 and 62 is determined respectively by distances DA1 and DA2 from the viewpoint position O. Signs 61P and 62P are projected images of each of the regions 61 and 62 in the projection plane 63. As described above, the viewpoint position O coincides with the viewpoint of the medical staff ST. Accordingly, the viewpoint position O is used as a reference to raise the visibility of the near side and lower the visibility of the far side, which is thought to be less discomforting. This also makes it possible to understand how deep each of the regions 61 and 62 is from the surface of the target area, as viewed from the viewpoint position O.

On the other hand, in FIGS. 26 to 29, the depth reference position is not the viewpoint position O but rather the surface position of the target area, and the depth is the distance extending from the surface position of the target area in the direction along the image-taking optical axis direction of the camera 13B.

First, the depth reference position in FIGS. 26 and 27 is the surface position of the target area that intersects projection lines set for each of the regions 61 and 62 when, in rendering each of the regions 61 and 62 as preparation information seen from the viewpoint position O side of the camera 13B, the projection plane 63 in which to project each of the regions 61 and 62 and a plurality of projection lines 64 connecting each of the plurality of regions 61 and 62 with the projection plane 63 are set virtually.

FIG. 26 is a modeling of perspective projection, and therefore the projection lines 64 are set virtually as straight lines extending to each of the regions 61 and 62, with the viewpoint position O as a base point. The projection line 64 connecting the region 61 with the projection plane 63 is the projection line 64Ba1, and the surface position of the target area that intersects the projection line 64Ba1 is the surface position SBa1 of the liver LV which is the target area. This surface position SBa1 is the depth reference position for the region 61, and the distance from the surface position SBa1 to the region 61 along the image-taking optical axis is the depth DBa1. Also, the projection line 64 connecting the region 62 with the projection plane 63 is the projection line 64Ba2, and the surface position of the target area that intersects the projection line 64Ba2 is the surface position SBa2 of the liver LV which is the target area. This surface position SBa2 is the depth reference position for the region 62, and the distance from the surface position SBa2 to the region 62 along the image-taking optical axis is the depth DBa2.

FIG. 27 is a modification of FIG. 26, and is a modeling of the example in FIG. 26 as a parallel projection. The projection lines 64 are set virtually as straight lines extending in parallel from the viewpoint position O side to each of the regions 61 and 62. The projection line 64 connecting the region 61 with the projection plane 63 is the projection line 64Bb1, and the surface position of the target area that intersects the projection line 64Bb1 is the surface position SBb1 of the liver LV which is the target area. This surface position SBb1 is the depth reference position for the region 61, and the distance from the surface position SBb1 to the region 61 along the image-taking optical axis is the depth DBb1. Also, the projection line 64 extending to the region 62 is the projection line 64Bb2, and the surface position of the target area that intersects the projection line 64Bb2 is the surface position SBb2 of the liver LV which is the target area. This surface position SBb2 is the depth reference position for the region 62, and the distance from the surface position SBb2 to the region 62 along the image-taking optical axis is the depth DBb2.

Next, in FIGS. 28 and 29, too, like in FIGS. 26 and 27, the depth reference position is not the viewpoint position O but rather the surface position of the target area, and the depth is the distance extending from the surface position of the target area in the direction along the image-taking optical axis direction of the camera 13B. The depth reference position in FIGS. 28 and 29 is the surface position of the target area that is closest from the viewpoint position O side of the camera 13B, and this point differs from FIGS. 26 and 27.

FIG. 28 is an example modeled by perspective projection. In FIG. 28, among the projection lines 64 connecting the target area with the projection plane 63, the projection line 64Ca intersects the closest surface position SCa of the target area (in this example, the liver LV). This surface position SCa serves as the depth reference position. That is, unlike FIGS. 26 and 27, in the example in FIG. 28, the depth reference position is set irrespectively of the regions 61 and 62. The depth of each of the regions 61 and 62 is determined respectively by distances DCa1 and DCa2 from the surface position SCa.

FIG. 29 is a modification of FIG. 28, and is an example of modeling the example in FIG. 28 by parallel projection.

In FIG. 29, the projection lines 64 extend in parallel from the projection plane 63 toward the target area along the image-taking optical axis. In the example in FIG. 29, the surface position of the target area that is closest from the viewpoint position O side of the camera 13B is the surface position SCb of the liver LV that intersects the projection line 64Cb. This surface position SCb serves as the depth reference position. The depth of each of the regions 61 and 62 is determined respectively by distances DCb1 and DCb2 from the surface position SCb.

Like in FIGS. 26 to 29, by taking the depth reference position to be the surface position of the target area as seen from the viewpoint position O side of the camera 13B, the depth of the target area from the surface position is understood more easily compared to the case of taking the reference position to be the viewpoint position O illustrated in FIG. 25.

Also, as illustrated in FIGS. 26 and 27, by taking the depth reference position to be the surface position of the target area that intersects with the projection lines 64 set for each of the regions 61 and 62 as preparation information, the depth of each of the regions 61 and 62 from the surface position is understood easily. More specifically, according to the examples in FIGS. 26 and 27, effects like the following are obtained. For example, in the case of excising a portion of a target area such as the liver LV, it may be desirable to understand how deeply a treatment tool needs to be pushed in after contacting the surface of the target area. According to FIGS. 26 and 27, the distance from the surface position of the target area is indicated for each of the regions 61 and 62, making it possible to understand how deep each region is from the surface position of the target area.

In contrast, as illustrated in FIGS. 28 and 29, by taking the depth reference position to be the closest surface position of the target area from the viewpoint position O side of the camera 13B, the depth of each of the regions 61 and 62 from the closest surface position is understood easily. Accordingly, in the examples illustrated in FIGS. 28 and 29, when the vascular structure 37 is displayed, the depth structure of each of the regions of the vascular structure 37 is understood easily as compared to FIGS. 26 and 27.

Figure 30:
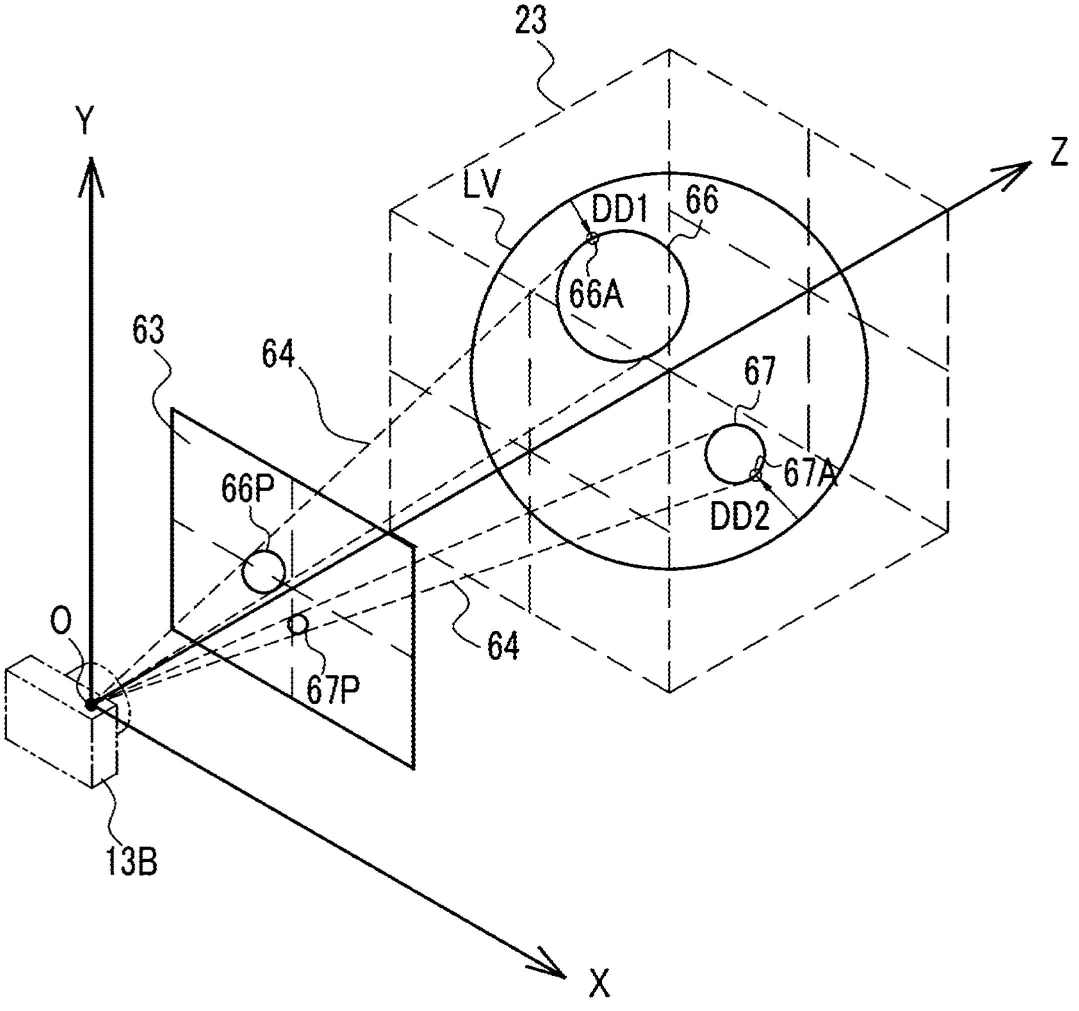
FIG. 30 is a diagram of a case of taking the surface position of a target area as a reference position irrespectively of the viewpoint position O.

FIG. 30 is an example of setting the depth direction irrespectively of the image-taking optical axis of the camera 13B. More specifically, FIG. 30 is a method of taking the depth direction to be the direction proceeding from the surface position to the deep layers, with the surface position of the target area in the preoperative preparation information 23 as a reference position. The preoperative preparation information 23 is a three-dimensional image based on the preoperative 3D image 34. The example in FIG. 30 illustrates a case in which the preoperative preparation information 23 contains the entire liver LV, and there are three-dimensional regions 66 and 67 within the liver LV. In this case, each of the regions 66 and 67 has a different depth from the surface position of the liver LV. Moreover, when viewing each of the regions 66 and 67 individually, the depth is also different depending on where the surface position is. In FIG. 30, signs DD1 and DD2 indicate the shortest distances from among the distances from the surface position of the liver LV to each of the regions 66 and 67. Namely, sign DD1 indicates the depth of the position 66A of shallowest depth from among the depths of the region 66. Also, sign DD2 indicates the depth of the position 67A of shallowest depth from among the depths of the region 67. Signs 66P and 67P are projected images, in the projection plane 63, of each of the regions 66 and 67.

According to the method illustrated in FIG. 30, the distances of each of the regions 66 and 67 from the surface position of the target area can be understood, regardless of the viewpoint position O. With the technique illustrated in FIG. 30, in the case of excising a portion on the surface layer side of the liver LV, for example, information such as how far from the surface position of the liver LV are blood vessels located is understood easily. Understanding where blood vessels are located makes it possible to perform excision and the like while avoiding blood vessels, for example. In this way, the technique illustrated in FIG. 30 is effective when performing a treatment such as excision or puncture on a target area.

Selectively Displaying Plurality of Information

Figure 31:
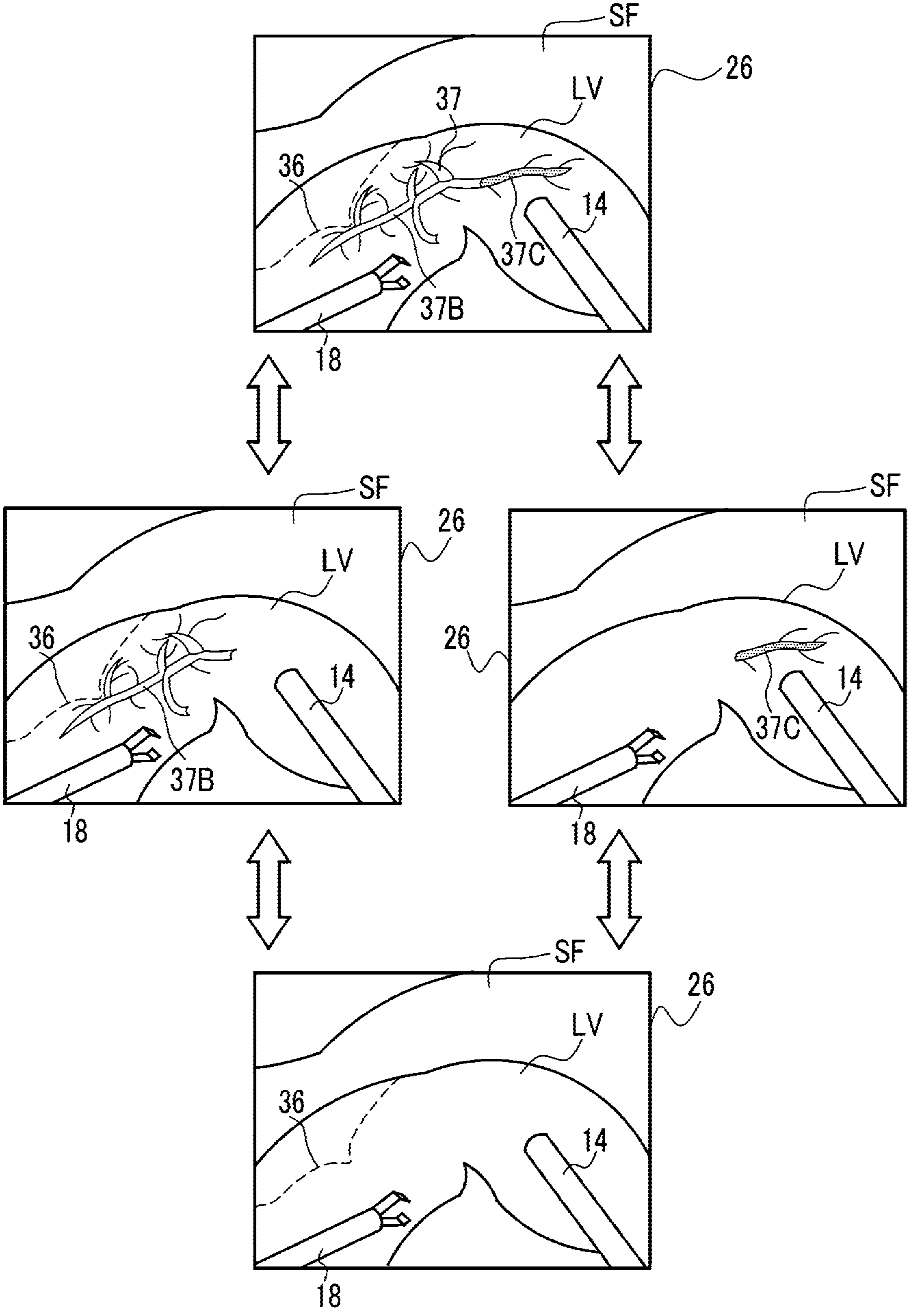
FIG. 31 is a diagram of an example in which information that differs by depth is displayed selectively.

As illustrated in FIG. 31, the processor 41 is also capable of causing a plurality of pieces of preoperative preparation information 23 at different depths to be displayed selectively in the composite image 26. Of the four composite images 26 illustrated in FIG. 31, first, in the composite image 26 in the upper row, the vascular structure 37, which contains both regions 37B and 37C at different depths, and the excision line 36 are displayed. In the composite image 26 on the left side in the middle row, the region 37C at a relatively deeper depth is not displayed, whereas conversely, in the composite image 26 on the right side in the middle row, only the region 37C is displayed, while the region 37B at a relatively shallower depth and the excision line 36 are not displayed. In the composite image 26 in the lower row, the vascular structure 37 is not displayed and only the excision line 36 is displayed. By enabling the selective displaying of information at different depths in this way, necessary information can be narrowed down from among a plurality of information at different depths.

Note that in regard to the condition for switching between display and non-display according to the depth of the preoperative preparation information 23 as illustrated in FIG. 31, the medical support apparatus 11 may switch to display or non-display according to depth when a switching instruction inputted via the reception device 42 is obtained. The medical support apparatus 11 may also acquire position information about the treatment tool 18 from the surgical field image 21 and switch to display or non-display on the basis of the position information about the treatment tool 18. For example, if the shortest distance between the treatment tool 18 and the surface position of the target area or the shortest distance between the treatment tool 18 and the vascular structure 37 or the excision line 36 is within a set distance set in advance, the medical support apparatus 11 may display preoperative preparation information 23 present within the set distance and not display preoperative preparation information 23 beyond the set distance. With this arrangement, when the treatment tool 18 approaches the vascular structure 37, for example, the vascular structure 37 is displayed to inform the medical staff ST about the possibility of contact between the treatment tool 18 and the vascular structure 37. That is, the specific value of the set distance is set on the basis of a distance at which the contact with the treatment tool 18 is considered to be a possibility. The set distance may be preset in the medical support apparatus 11, and may also be set or changed via the reception device 42.

Examples of Preoperative Preparation Information

Figure 32:
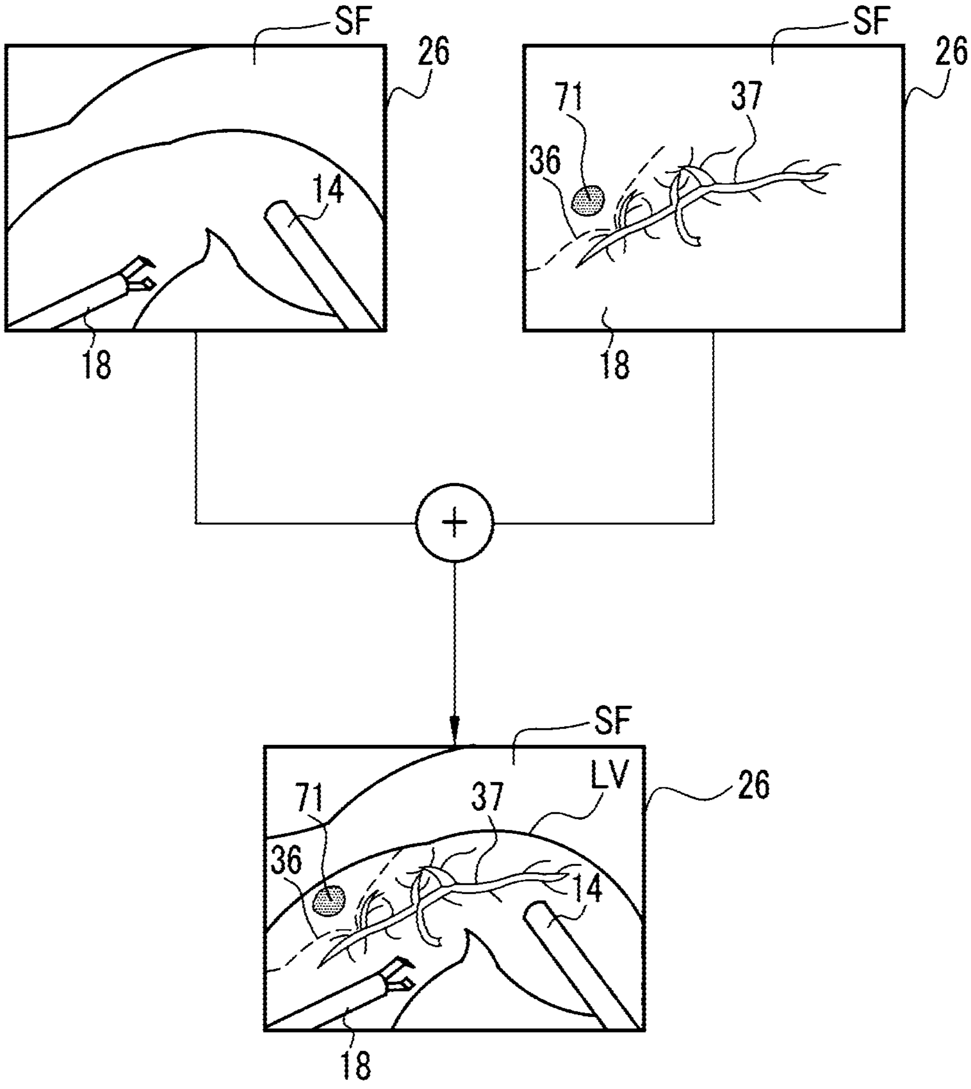
FIG. 32 is a diagram of an example in which a lesion is displayed as preoperative preparation information.

The preoperative preparation information 23 is not limited to the excision line 36 and the vascular structure 37, and may also include other information. In the example illustrated in FIG. 32, the preoperative preparation information 23 includes a lesion 71 such as a tumor. In the composite image 26, the lesion 71 is displayed in addition to the excision line 36 and the vascular structure 37. The lesion 71 includes tumors, calcified regions, hemorrhagic regions, and the like.

Figure 33A:
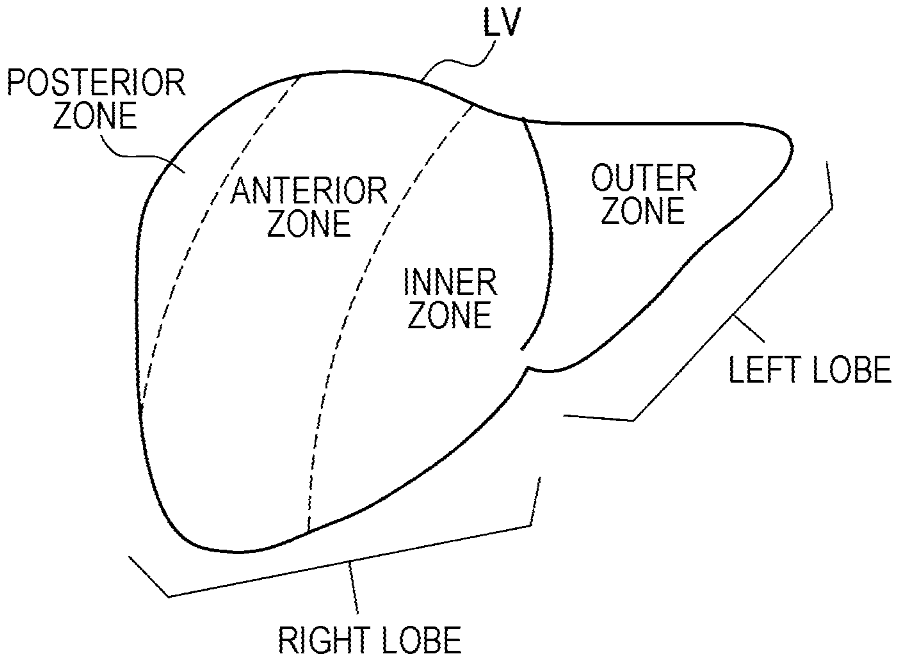
FIGS. 33A and 33B are diagrams illustrating anatomical regions of the liver.
Figure 33B:
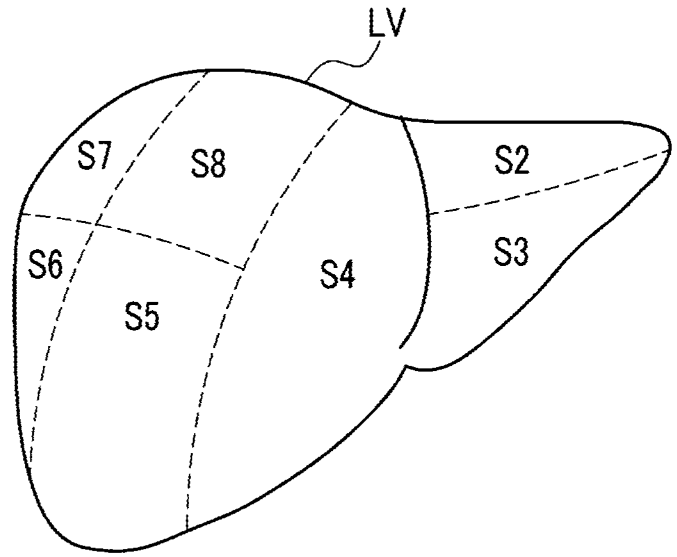

Also, as illustrated in FIGS. 33A and 33B, anatomical regions subdividing the liver LV may also be displayed. In FIG. 33A, a left lobe, a right lobe, and zones subdividing the left and right lobes are illustrated as anatomical regions subdividing the liver LV. The zones are an outer zone, an inner zone, an anterior zone, a posterior zone, and the like. Also, in FIG. 33B, eight sub-zones S1 to S8 further subdividing each of the zones are illustrated. Note that in FIGS. 33A and 33B, S1 is obscured and therefore not illustrated. Such anatomical regions may also be included in the preoperative preparation information 23. Such anatomical regions are an example of “reference information” when determining the excision line 36.

By displaying the reference information in addition to the excision line 36 in the composite image 26, effects like the following can be expected. Namely, when the liver LV is deformed under the influence of insufflation or the like, the excision line 36 may be displayed out of alignment with the corresponding position within the surgical field image 21. In this case, if the anatomical regions used as reference information when determining the excision line 36 are displayed in addition to the excision line 36, the medical staff ST may be able to estimate the appropriate position of the excision line 36 by confirming the positions of the anatomical regions, even if the display position of the excision line 36 is misaligned due to deformation of the liver LV. Besides the anatomical regions illustrated in FIGS. 33A and 33B, the vascular structure 37 and the lesion 71 may also be included as reference information when determining the excision line 36.

Example of Target Area

Figure 34:
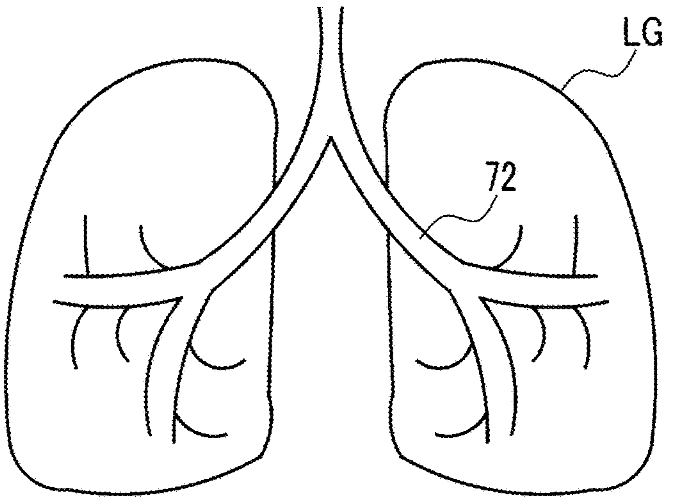
FIG. 34 is a diagram of the lungs.

As illustrated in FIG. 34, the target area is not limited to the liver LV and may also be lung LG. In the case of the lung LG, the internal structure is a bronchial structure 72, for example. Additionally, the target area may also be another organ other than the lung LG or the liver LV, and may be any anatomical area inside the body.

Modification of Ultrasound Probe

In the above example, an ultrasound probe of the convex type is described as an example of the ultrasound probe 14, but an ultrasound probe of the linear type with a flat transmitting/receiving surface for transmitting and receiving the ultrasonic waves of the ultrasonic transducer 14B may also be used. The transmitting/receiving surface may also be of the radial type disposed in the circumferential direction around the axis of the ultrasound probe 14.

Figure 35:
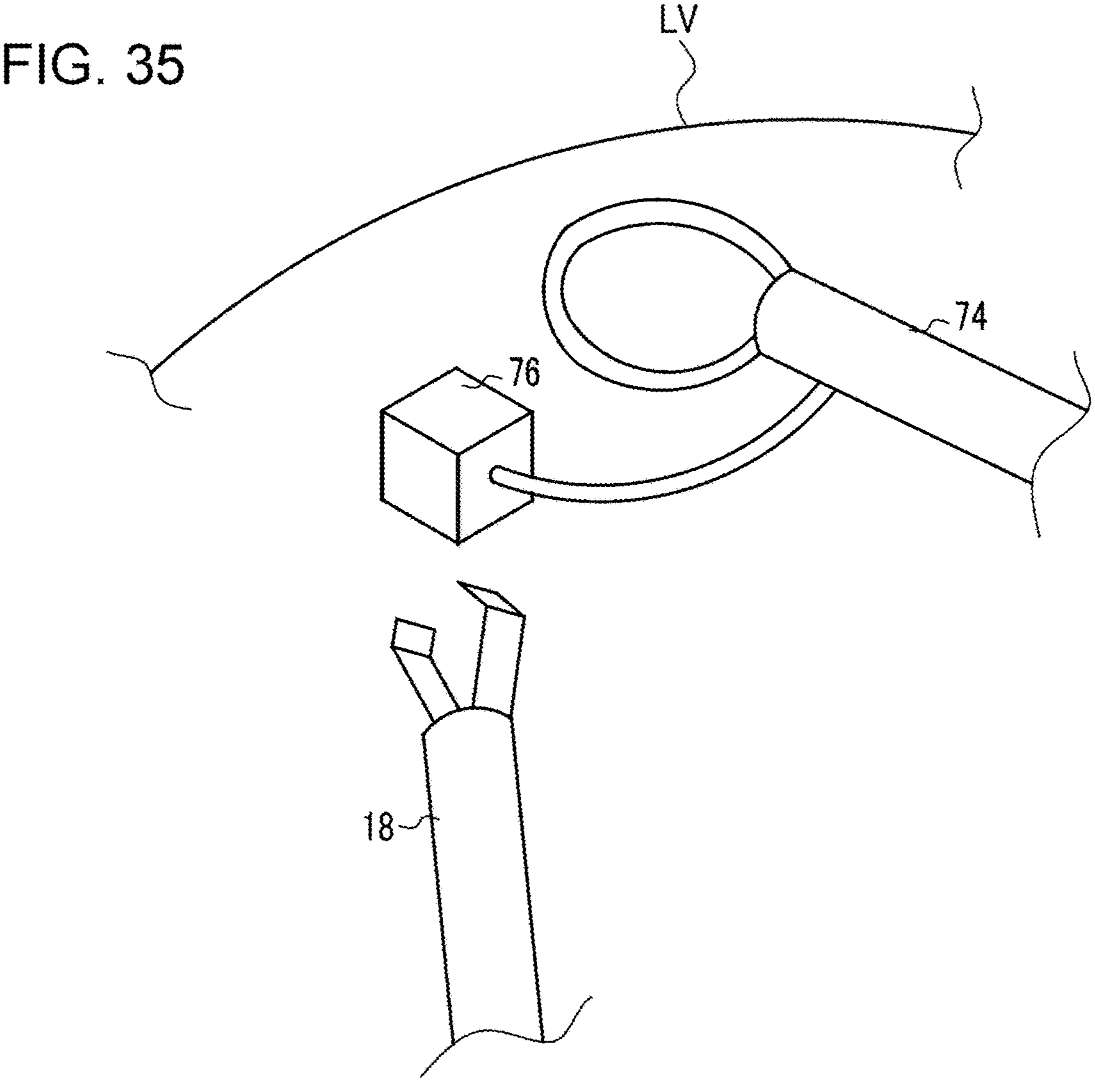
FIG. 35 is a diagram of a compact ultrasound probe.

Also, as illustrated in FIG. 35, a compact ultrasound probe 76 attached to a treatment tool 7 such as a snare 74 may also be used. The ultrasound probe 76 is attached to the snare 74 by a wire, for example. When the ultrasound probe 76 is used to scan the surface of the target area, a treatment tool 18 such as forceps is used to grip the ultrasound probe 76 and move the ultrasound probe 76 in the gripped state.

Also, the above describes an example of using the medical support apparatus 11 in specular surgery, but usage is not limited thereto, and the medical support apparatus 11 may also be used when the main purpose of the examination is to observe a target area inside the body. Preparation information that is prepared prior to examination is used as the preparation information to be superimposed onto the surgical field image 21. Also, the surgical field image 21 means an image taken of the surgical field SF including a target area of examination instead of, or in addition to, an image taken of the surgical field SF including a target area of surgery.

Displaying an internal structure of a target area during an examination has merits like the following. For example, if a tumor internal to the liver LV is represented in a tomographic image taken with a CT apparatus but is difficult to find taking images with an ultrasound probe, the tumor is displayed as the preoperative preparation information 23 in the liver LV in the surgical field image 21 during an examination performed with the ultrasound probe 14. This allows for guidance to the position corresponding to the tumor to be scanned by the ultrasound probe 14. This also allows for guidance to a puncture position of a puncture needle for puncturing the tumor when doing a biopsy of the tumor.

The above describes a rigid endoscope with an inflexible insertion part as the endoscope 13, but the endoscope 13 may also be a flexible endoscope with a flexible insertion part.

Also, the above describes an example of using the medical support apparatus 11 in specular surgery, but the medical support apparatus 11 may also be used in abdominal surgery. In the case of abdominal surgery, the camera that takes images of the surgical field is not a camera built into an endoscope, but instead is a camera installed above the operating table, such as a camera installed on the ceiling of the operating room, for example.

The above describes the surgical field SF inside the abdominal cavity as an example of a surgical field inside the body, but the inside of the body is not limited to the inside of the abdominal cavity and may also be a body cavity other than the abdominal cavity, such as the thoracic cavity, and may also be the upper gastrointestinal tract such as the esophagus, the lower gastrointestinal tract such as the intestines, or inside a tube such as the bronchial tubes. In the case of applying the technology of the present disclosure to a surgical field inside a tube, a camera built into an endoscope inserted into the bronchial tubes is used as the camera, for example. The medical support apparatus then uses the camera of the endoscope to acquires a surgical field image taken of the surgical field, including a target area inside the tube and an ultrasound probe inserted into the tube through a forceps channel of the endoscope.

The above describes a CT apparatus, MRI apparatus, and the like as an example of the tomograph that takes the tomographic image group to serve as the basis for the preoperative preparation information 23, but the tomograph may also be an ultrasound probe. For example, an ultrasound image group 22 may be acquired in advance prior to surgery, separately from the ultrasound image group 22 to be acquired during surgery, and the preoperative preparation information 23 may be created on the basis of the acquired ultrasound image group 22. Besides an ultrasound probe, an optical coherence tomography (OCT) probe may also be used.

Also, the second embodiment above may be combined with the first embodiment or be independent from the first embodiment. The following technologies can be understood as technologies in which the second embodiment is independent from the first embodiment.

[Appendix 1] A medical support apparatus comprising a processor configured to:

acquire a surgical field image obtained by optically taking, with a camera, an image of a surgical field containing a target area inside the body;

generate a composite image with preparation information superimposed onto the surgical field image, the preparation information having been prepared in advance as information related to the target area, including at least a three-dimensional image illustrating an internal structure of the target area or applied information applied to the three-dimensional image, and having a defined three-dimensional position within the three-dimensional image; and control displaying of the composite image, wherein if the preparation information further includes a plurality of pieces of preparation information at different depths in a depth direction proceeding from a surface layer to deep layers of the target area in the three-dimensional image, the processor is configured to change a display appearance of the plurality of pieces of preparation information in the composite image, depending on the depth.

[Appendix 2] The medical support apparatus according to appendix 1, wherein when changing the display appearance, the processor is configured to raise the visibility of the preparation information nearer the surface layer than the deep layers.

[Appendix 3] The medical support apparatus according to appendix 1 or appendix 2, wherein the depth direction is the direction along an image-taking optical axis of the camera that takes the surgical field image.

[Appendix 4] The medical support apparatus according to appendix 3, wherein a reference position for the depth is a viewpoint position of the camera.

[Appendix 5] The medical support apparatus according to appendix 3, wherein a reference position for the depth is a surface position of the target area.

[Appendix 6] The medical support apparatus according to appendix 5, wherein if, when rendering the preparation information as seen from the viewpoint position side of the camera, a projection plane in which to project the preparation information and a plurality of projection lines connecting each of the plurality of pieces of preparation information with the projection plane are set virtually, the reference position for the depth is a surface position of the target area that intersects the projection line set for each piece of the preparation information.

[Appendix 7] The medical support apparatus according to appendix 5, wherein the reference position for the depth is a surface position of the target area that is closest from the viewpoint position side of the camera.

[Appendix 8] The medical support apparatus according to appendix 1, wherein the depth direction is the direction proceeding from a surface position to the deep layers, with the surface position of the target area in a second three-dimensional image as a reference position.

[Appendix 9] The medical support apparatus according to any one of appendices 1 to 8, wherein the surgical field image is an image acquired in the camera in specular surgery, and the camera is a camera provided at a distal end part of an endoscope.

[Appendix 10] The medical support apparatus according to any one of appendices 1 to 9, wherein the preparation information includes at least one from among an excision line where the target area is to be excised, a lesion, a vascular structure which is an internal structure of the target area, and reference information when determining the excision line.

[Appendix 11] The medical support apparatus according to any one of appendices 1 to 10, wherein the target area is the lung or the liver.

[Appendix 12] An operating method for a medical support apparatus comprising a processor, the operating method causing the processor to:

acquire a surgical field image obtained by optically taking, with a camera, an image of a surgical field containing a target area inside the body;

generate a composite image with preparation information superimposed onto the surgical field image, the preparation information having been prepared in advance as information related to the target area, including at least a three-dimensional image illustrating an internal structure of the target area or applied information applied to the three-dimensional image, and having a defined three-dimensional position within the three-dimensional image; and control displaying of the composite image, wherein if the preparation information further includes a plurality of pieces of preparation information at different depths in a depth direction proceeding from a surface layer to deep layers of the target area in the three-dimensional image, the processor is configured to change a display appearance of the plurality of pieces of preparation information in the composite image.

[Appendix 13] An operating program for causing a computer to function as a medical support apparatus, the operating program of the medical support apparatus causing the computer to execute processing to:

acquire a surgical field image obtained by optically taking, with a camera, an image of a surgical field containing a target area of surgery inside a body cavity;

generate a composite image with preparation information superimposed onto the surgical field image, the preparation information having been prepared in advance prior to surgery as information related to the target area, including at least a three-dimensional image illustrating an internal structure of the target area or applied information applied to the three-dimensional image, and having a defined three-dimensional position within the three-dimensional image; and control displaying of the composite image, wherein if the preparation information further includes a plurality of pieces of preparation information at different depths in a depth direction proceeding from a surface layer to deep layers of the target area in the three-dimensional image, the computer executes processing to change a display appearance of the plurality of pieces of preparation information in the composite image.

Also, in the embodiments above, any of the various types of processors indicated below can be used as the hardware structure of a processing unit that executes various processes, such as those of the image acquisition unit, the positional relationship information derivation unit, the composite image generation unit, and the display control unit. The various types of processors include: a central processing unit (CPU), which is a general-purpose processor that executes software (a program or programs) to function as any of various processing units; a programmable logic device (PLD) whose circuit configuration is modifiable after fabrication, such as a field-programmable gate array (FPGA); and a dedicated electric circuit, which is a processor having a circuit configuration designed for the specific purpose of executing a specific process, such as an application-specific integrated circuit (ASIC).

Also, the various processes above may be executed by one of these various processors, or by a combination of two or more processors of the same or different types (such as multiple FPGAs, or a combination of a CPU and an FPGA, for example). Moreover, multiple processing units may also be configured as a single processor. One example of configuring multiple processing units as a single processor is a mode utilizing a processor in which the functions of an entire system, including the plurality of processing units, are achieved on a single integrated circuit (IC) chip, such as a system on a chip (SoC).

In this way, various types of processing units are configured as a hardware structure by using one or more of the various types of processors indicated above.

More specifically, circuitry combining circuit elements such as semiconductor elements can be used as the hardware structure of these various types of processors.

Additionally, the technology of the present disclosure also extends to an operating program for a medical support apparatus as well as to a computer-readable storage medium (such as USB memory or Digital Versatile Disc Read-Only Memory (DVD-ROM)) that non-transiently stores an operating program for a medical support apparatus.

The descriptions and illustrations given above are detailed descriptions of portions related to the technology of the present disclosure, and are nothing more than examples of the technology of the present disclosure. For example, the above descriptions pertaining to configuration, function, action, and effect are descriptions pertaining to one example of the configuration, function, action, and effect of portions related to the technology of the present disclosure. Needless to say, unnecessary portions may be deleted and new elements may be added or substituted with respect to the descriptions and illustrations given above, insofar as the result does not depart from the gist of the technology of the present disclosure. Also, to avoid confusion and to facilitate understanding of the portions related to the technology of the present disclosure, in the descriptions and illustrations given above, description is omitted in regard to common technical knowledge and the like that does not require particular explanation to enable implementation of the technology of the present disclosure.

In this specification, "A and/or B" is synonymous with "at least one of A or B". That is, "A and/or B" means that: A only is a possibility; B only is a possibility; and a combination of A and B is a possibility. Also, in this specification, the same way of thinking as for "A and/or B" also applies when three or more matters are expressively linked using "and/or".

All documents, patent applications, and technical standards mentioned in this specification are incorporated by reference herein to the same extent that individual documents, patent applications, and technical standards are specifically and individually noted as being incorporated by reference.

What is claimed is:

1. A medical support apparatus comprising a processor configured to:

acquire a surgical field image obtained by optically taking, with a camera, an image of a surgical field that contains a target area inside the body and an ultrasound probe inserted into the body;

acquire a first three-dimensional image illustrating an internal structure of the target area, the first three-dimensional image being based on an ultrasound image group taken by the ultrasound probe;

derive first positional relationship information indicating a position and orientation of the first three-dimensional image within the surgical field image, on the basis of pose information that indicates a position and orientation of the ultrasound probe within the surgical field as estimated by image analysis of the surgical field image, by estimating the position and orientation of the ultrasound probe within the surgical field from the surgical field image and determining the position and orientation of the first three-dimensional image within the surgical field image by expressing the first three-dimensional image in a coordinate system of the ultrasound probe and transforming that coordinate system into a coordinate system of the surgical field image using the estimated pose;

acquire a second three-dimensional image illustrating the internal structure of the target area and having been generated on the basis of a tomographic image group taken in advance by a tomograph;

derive second positional relationship information indicating a positional relationship between a position within the first three-dimensional image and a position within the second three-dimensional image by performing image analysis on the first three-dimensional image and the second three-dimensional image, the image analysis associating morphologies of an internal structure common to both images and computing a three-dimensional transformation between coordinate systems of the first and second three-dimensional images;

generate a composite image comprising the surgical field image and preparation information, the preparation information having been prepared in advance as information related to the target area, including at least the second three-dimensional image or applied information applied to the second three-dimensional image, and having a defined three-dimensional position within the second three-dimensional image, placing the preparation information at a position that corresponds to the target area within the surgical field image by transforming its three-dimensional position using the second positional relationship information followed by the first positional relationship information; and control displaying of the composite image, wherein the internal structure common to both images includes a vascular structure, and wherein, to derive the second positional relationship information, the processor is configured to:

extract the vascular structure from each of the first three-dimensional image and the second three-dimensional image, compare bifurcation points of blood vessels included in the extracted vascular structures in the first and second three-dimensional images, extract a topological structure of the vascular structure including at least a number of bifurcation points, the topological structure maintaining identity even when the vascular structure is deformed while preserving continuity, and retrieve, based on the topological structure, from the vascular structure extracted from the second three-dimensional image, a portion similar to the vascular structure extracted from the first three-dimensional image, thereby mitigating effects of real-time deformations.

2. The medical support apparatus according to claim 1, wherein a marker formed from an optically detectable pattern is provided on an outer circumferential surface of the ultrasound probe, and the processor is configured to estimate the position and orientation of the ultrasound probe by detecting the marker from the surgical field image.

3. The medical support apparatus according to claim 1, wherein the processor is configured to acquire deformation information indicating how the internal structure in the first three-dimensional image is deformed with respect to the internal structure in the second three-dimensional image, the second three-dimensional image having been prepared in advance as a preoperative three-dimensional image, deform the preparation information based on the acquired deformation information, and generate the composite image with the deformed preparation information superimposed onto the surgical field image.

4. The medical support apparatus according to claim 3, wherein the target area comprises a region in a lung or in a liver.

5. The medical support apparatus according to claim 1, wherein the preparation information includes a plurality of pieces of preparation information at different depths in a depth direction proceeding from a surface layer to deep layers of the target area in the second three-dimensional image.

6. The medical support apparatus according to claim 5, wherein, when superimposing the plurality of pieces of preparation information at different depths onto the surgical field image, the processor is configured to change a display appearance of the plurality of pieces of preparation information in the composite image, depending on the depth.

7. The medical support apparatus according to claim 6, wherein when changing the display appearance, the processor is configured to raise visibility of the preparation information nearer the surface layer than the deep layers.

8. The medical support apparatus according to claim 6, wherein the depth direction is the direction along an image-taking optical axis of the camera that takes the surgical field image.

9. The medical support apparatus according to claim 8, wherein a reference position for the depth is a viewpoint position of the camera.

10. The medical support apparatus according to claim 8, wherein a reference position for the depth is a surface position of the target area.

11. The medical support apparatus according to claim 10, wherein, when rendering the preparation information as seen from a viewpoint position of the camera, the processor virtually sets a projection plane for projecting the preparation information and a plurality of projection lines each connecting a respective one of the plurality of pieces of preparation information to the projection plane, and the reference position for the depth is a surface position of the target area that intersects the respective projection line set for each piece of the preparation information.

12. The medical support apparatus according to claim 10, wherein the reference position for the depth is a surface position of the target area that is closest from the viewpoint position side of the camera.

13. The medical support apparatus according to claim 6, wherein the depth direction is the direction proceeding from a surface position to the deep layers, with the surface position of the target area in a second three-dimensional image as a reference position.

14. The medical support apparatus according to claim 5, wherein the depth direction is the direction proceeding from a surface position to the deep layers, with the surface position of the target area in a second three-dimensional image as a reference position.

15. The medical support apparatus according to claim 1, wherein the surgical field image is an image acquired in the camera in specular surgery, and the camera is a camera provided at a distal end part of an endoscope.

16. The medical support apparatus according to claim 1, wherein the preparation information includes at least one from among an excision line where the target area is to be excised, a lesion, a vascular structure which is an internal structure of the target area, and reference information when determining the excision line.

17. An operating method for a medical support apparatus comprising:

acquiring a surgical field image obtained by optically taking, with a camera, an image of a surgical field that contains a target area inside the body and an ultrasound probe inserted into the body;

acquiring a first three-dimensional image illustrating an internal structure of the target area, the first three-dimensional image being based on an ultrasound image group taken by the ultrasound probe;

deriving first positional relationship information indicating a position and orientation of the first three-dimensional image within the surgical field image, on the basis of pose information that indicates a position and orientation of the ultrasound probe within the surgical field as estimated by image analysis of the surgical field image, by estimating the position and orientation of the ultrasound probe within the surgical field from the surgical field image and determining the position and orientation of the first three-dimensional image within the surgical field image by expressing the first three-dimensional image in a coordinate system of the ultrasound probe and transforming that coordinate system into a coordinate system of the surgical field image using the estimated pose;

acquiring a second three-dimensional image illustrating the internal structure of the target area and having been generated on the basis of a tomographic image group taken in advance by a tomograph;

deriving second positional relationship information indicating a positional relationship between a position within the first three-dimensional image and a position within the second three-dimensional image by performing image analysis on the first three-dimensional image and the second three-dimensional image, the image analysis associating morphologies of an internal structure common to both images and computing a three-dimensional transformation between coordinate systems of the first and second three-dimensional images;

generating a composite image comprising the surgical field image and preparation information, the preparation information having been prepared in advance as information related to the target area, including at least the second three-dimensional image or applied information applied to the second three-dimensional image, and having a defined three-dimensional position within the second three-dimensional image, placing the preparation information at a position that corresponds to the target area within the surgical field image by transforming its three-dimensional position using the second positional relationship information followed by the first positional relationship information; and controlling displaying of the composite image, wherein the internal structure common to both images includes a vascular structure, and wherein deriving the second positional relationship information comprises:

extracting the vascular structure from each of the first three-dimensional image and the second three-dimensional image, comparing bifurcation points of blood vessels included in the extracted vascular structures in the first and second three-dimensional images, extracting a topological structure of the vascular structure including at least a number of bifurcation points, the topological structure maintaining identity even when the vascular structure is deformed while preserving continuity, and retrieving, based on the topological structure, from the vascular structure extracted from the second three-dimensional image, a portion similar to the vascular structure extracted from the first three-dimensional image, thereby mitigating effects of real-time deformations.

18. A non-transitory computer-readable storage medium storing an operating program for causing a computer to function as a medical support apparatus, the operating program of the medical support apparatus causing the computer to perform the method of claim 17.

* * * * *